United States Patent [19]
Northway-Meyer

[11] Patent Number: 4,848,331
[45] Date of Patent: Jul. 18, 1989

[54] APPARATUS AND METHOD FOR PULMONARY VENTILATION OF A PATIENT CONCURRENT WITH FIBEROPTIC RESPIRATORY TRACT EXAMINATION AND TRACHEAL INTUBATION

[76] Inventor: Robert Northway-Meyer, 5625 NE. Windermere Rd., Seattle, Wash. 98105

[21] Appl. No.: 930,696

[22] Filed: Nov. 14, 1986

[51] Int. Cl.$^4$ ............................................. A61M 16/00
[52] U.S. Cl. ........................... 128/200.26; 128/206.29; 128/207.14
[58] Field of Search ....................... 128/200.26, 201.26, 128/202.28, 203.29, 205.25, 206.21, 206.28, 206.29, 207.14, 207.15, 207.17, 207.18

[56] References Cited

U.S. PATENT DOCUMENTS

| | | | |
|---|---|---|---|
| 3,756,244 | 9/1973 | Kinnear et al. | 128/207.14 |
| 3,774,616 | 11/1973 | White et al. | |
| 3,905,361 | 9/1975 | Hewson et al. | 128/207.15 |
| 4,256,099 | 3/1981 | Dryden | 128/207.15 |
| 4,270,531 | 6/1981 | Blachly et al. | 128/207.14 |
| 4,497,318 | 2/1985 | Donmichael | 128/207.15 |
| 4,506,665 | 3/1985 | Andrews et al. | 128/203.29 |

OTHER PUBLICATIONS

Olympus LF-1 Tracheal Intubation Fiberscope, 8/1/86.
Bay Medical Inc., p. 46, Fall '86.
Patil-Syracuse Oral Airway, 8/25/85.
Fiberoptic Laryngoscope Guide and Protector, Wang, Jan.–Feb. 1977.
New Airway Intubator Advocated for Blind . . . , May 1983.

Primary Examiner—Max Hindenburg
Assistant Examiner—John P. Lacyk
Attorney, Agent, or Firm—T. W. Secrest

[57] ABSTRACT

This invention comprises an apparatus used by an anesthesiologist in anesthetizing a patient. The apparatus comprises oral airways, oral masks and a face mask and combinations of these. There is disclosed some of the development of apparatus in anesthesiology and there is disclosed some of the object and advantages of the invention. With this apparatus it is possible to have fiberoptic respiratory tract examination and tracheal intubation.

30 Claims, 24 Drawing Sheets

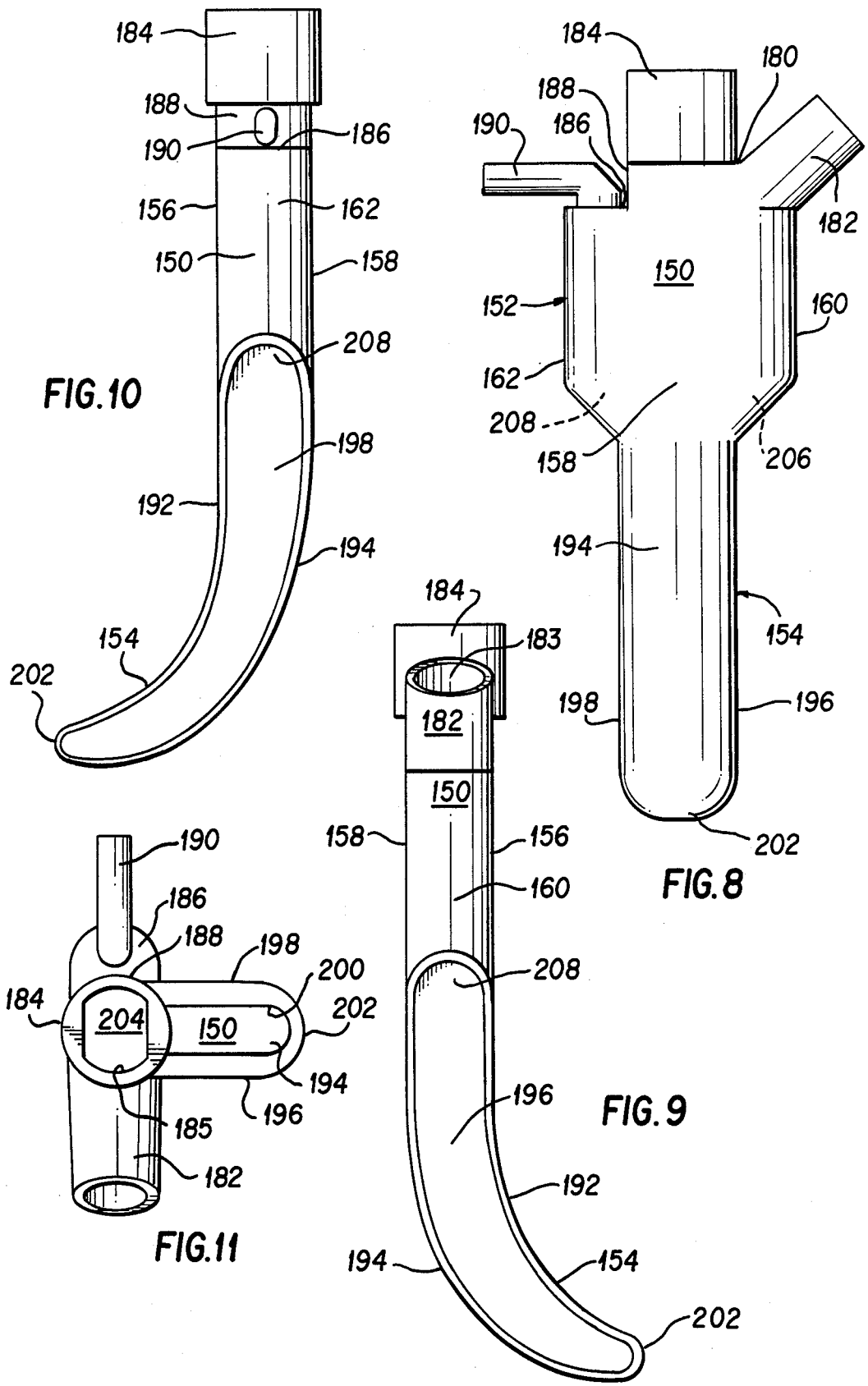

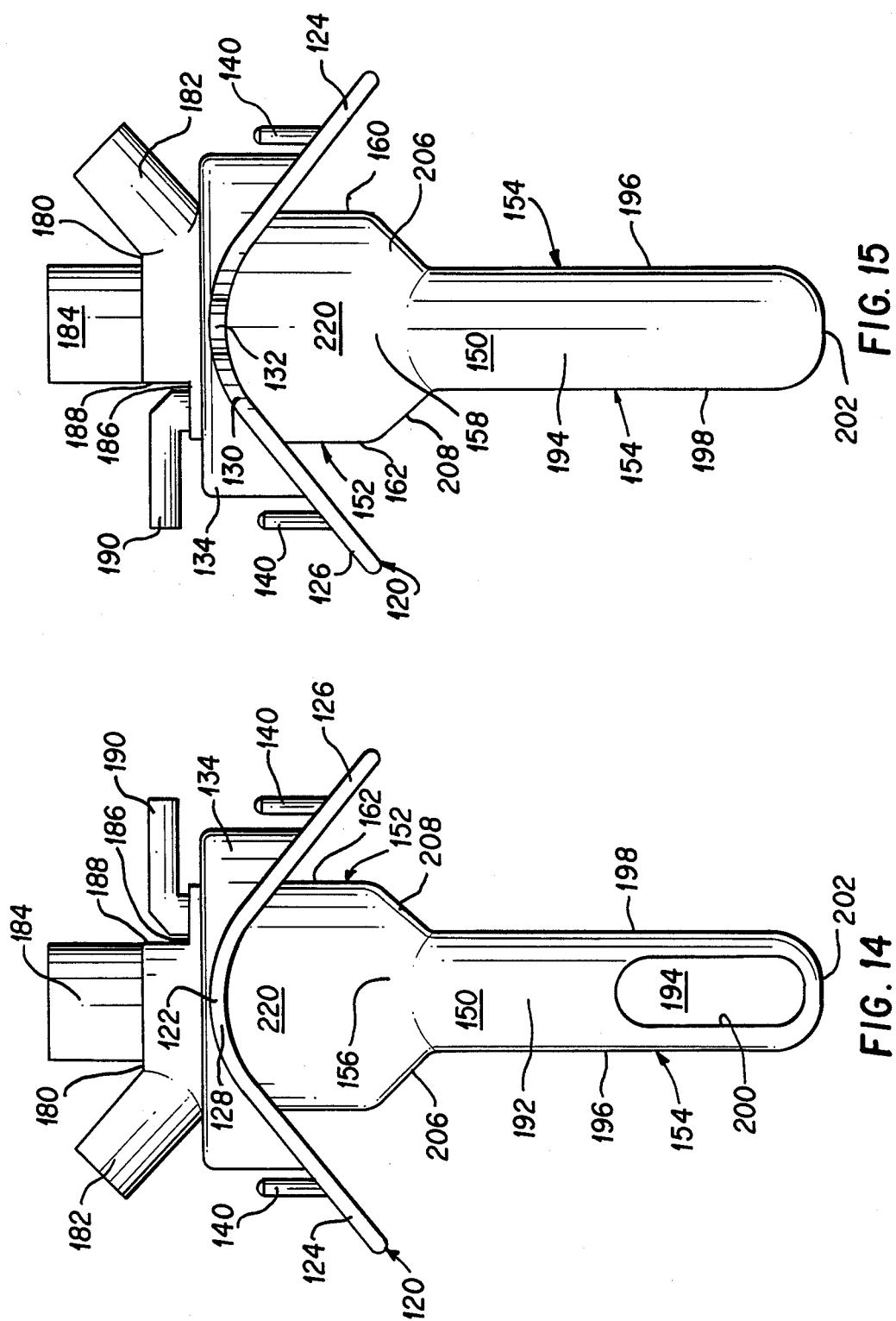

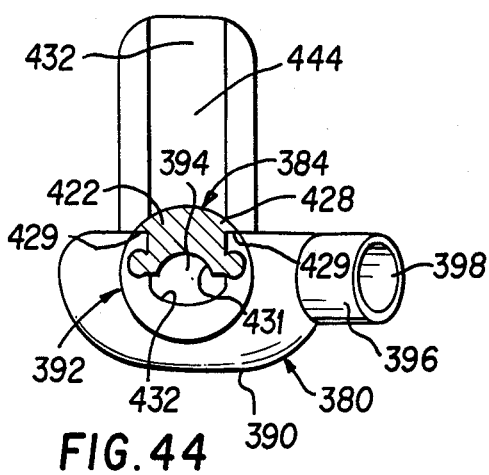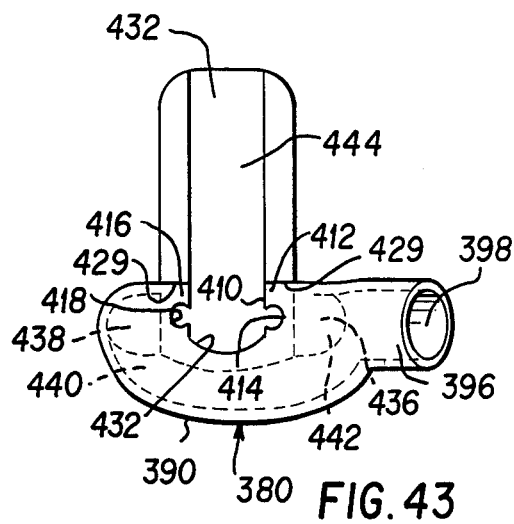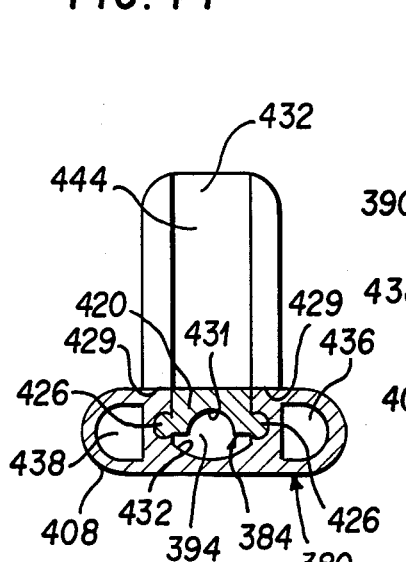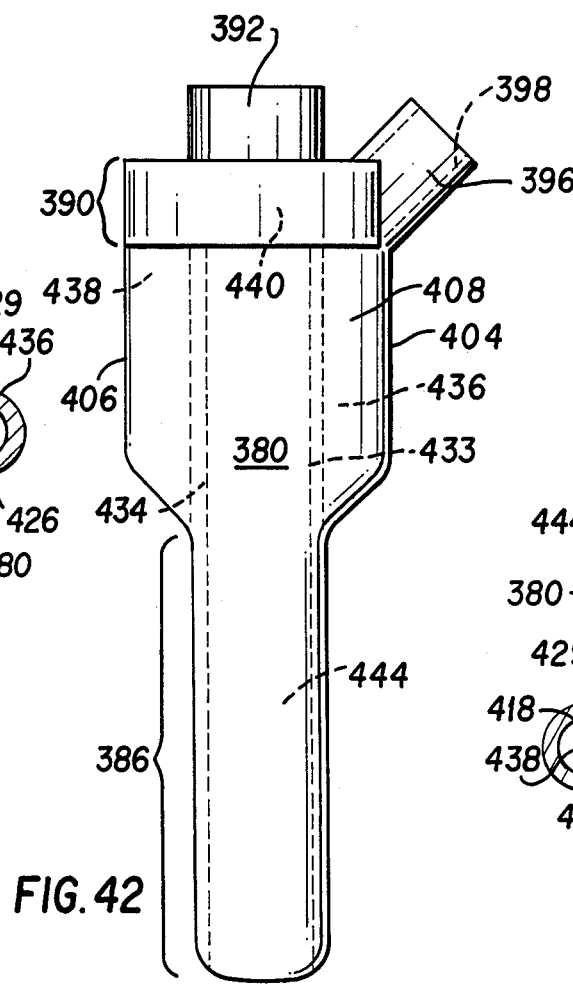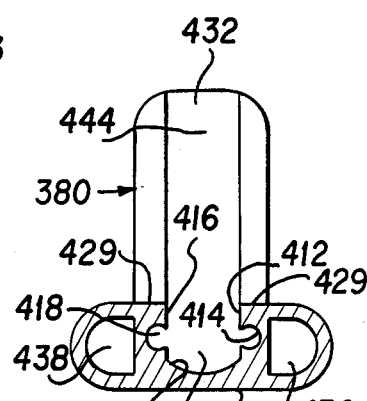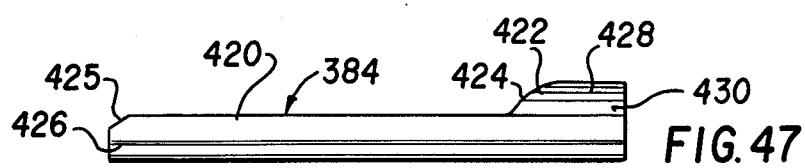

APPARATUS AND METHOD FOR PULMONARY VENTILATION OF A PATIENT CONCURRENT WITH FIBEROPTIC RESPIRATORY TRACT EXAMINATION AND TRACHEAL INTUBATION

THE BACKGROUND OF THE INVENTION

Intubation of the trachea (in animals) was described as early as 1543. The first attempts in humans, starting in the early 1700's were made, for resusciation of drowning victims. Later efforts starting in 1858 were made to prevent aspiration pneumonia in surgery of the upper air-passages under local anesthesia. The first intubation under general anesthesia was performed in 1878.

Improvements in equipment and techniques followed, especially during and after World War I, when plastic surgery and jaw injuries made endotracheal anesthesia mandatory for proper control of the patient's airway under general anesthesia.

The introduction of curare in 1942, for muscle relaxation under general anesthesia, increased the incidence of hypoventilation and apnea, and necessitated the development of intermittent positive pressure ventilation to deal with these problems. The advent of mechanical ventilators made the use of endotracheal tubes obligatory.

Endotracheal anesthesia is now standard and accepted practice for all major surgery under general anesthesia. It provides much safer anesthesia for the patient and greatly improves operating conditions for the surgeon.

In spite of the many advances in techniques and equipment, however, certain patients, classed as 'THE DIFFICULT INTUBATION' or 'THE DIFFICULT AIRWAY' present themselves from time to time both in the elective and in the emergency stiuation. They are the nightmare of every practitioner and for some their 'Waterloo'.

In a recent article in the Journal of American Medical Association (253.16), April 26, 1985, Keenan and Bogan cite failure to ventilate the patient as responsible for half of the cases of cardiac arrest under anesthesia. The causes for failure to ventilate include failure to adequately ventilate by mask or after improper intubation (esophageal or right mainstem bronchus), and inability to intubate or ventilate.

The causes of 'DIFFICULT INTUBATION' are many, including:

(1) Tumors of the vocal cords or nearby structures.

(2) Large, floppy epiglottis; acute epiglottitis; epiglottic tumor.

(3) Large, thick tongue, tumors of the tongue, enlarged tonsils.

(4) Submandibular abscess; pharyngeal abscess (Ludwig's Angina).

(5) Extreme obesity.

(6) Short, muscular neck; thyroid enlargement; cystic hygroma.

(7) Burn contractures of the neck.

(8) Long, high-arched palate associated with a long, narrow mouth.

(9) Increased alveolar-mental distance which necessitates wide opening of the mandible for laryngoscopy.

(10) Inadequate relaxation under anesthesia with inability to open mouth widely.

(11) Mandibular problems include: Short mandible (mandibular hypoplasia with receding jaw and obtuse mandibular angles); degenerative arthritis and ankylosis of the temporomandibular joint with inability to open the mouth widely (poor mobility of the mandible).

(12) Dental problems include: Loose or snaggy teeth; prominent large teeth (usually a full set); protruding upper incisor teeth associated with relative overgrowth of the premaxilla; dental malocclusion.

(13) Spinal problems include: Limited mobility of the head and neck due to ankylosing spondylitis; degenerative arthritis; fractured cervical with spinal cord injury (either actual or potential) (e.g. cord compression, etc.); patients in 'HALO' traction.

(14) 'Anterior Glottis'; small glottic opening; laryngeal edema.

(15)Tracheal stenosis; undersized trachea; tracheoesophageal fistula (in adults).

(16) Pneumothorax.

(17) Thoracic aortic aneurysm.

During difficult intubations under routine laryngoscopy in elective surgical patients or in the emergency situation, when all else has failed, the harried anesthesiologists, at last, thinks of the flexible fiberoptic scope (FSS), but, owing to lack of experience and an effective ventilating/intubating airway is frequently unable to use the fiberoptic device properly. Added to this is the fact that frequent suctioning of secretions and/or blood from the oropharynx resulting from difficult routine laryngoscopy leads to unwanted interruption of ventilation which may have deleterious effects (such as hypoxemia) if persisted in too long.

The expensive fiberoptic device may then be thrust aside in disgust. Too bad, because it's an extremely useful instrument. Previous practice with the fiberoptic ventilating airway and the fiberoptic scope could have turned the failures into enthusiastic successes.

In an effort to solve the problems of the 'DIFFICULT INTUBATION' various devices and techniques have been developed over the years: laryngoscopes of different sizes and shapes, prisms, intubating airways, tube introducers, controllable-tip endotracheal tubes, tube benders and tube elevators, stylets to alter the curvature of the ET tube, stylets to act as guides for the ET tube, etc. Each one had merit, but the problems still remained.

DESCRIPTION OF THE PRIOR ART

Several intubating airways were compared with the present invention. They include the English DIVIDED AIRWAY, the Williams AIRWAY INTUBATOR, and The Berman INTUBATING PHARYNGEAL AIRWAY. Although each is a useful aid in tracheal intubation, none has the built-in capacity to ventilate the patient, especially the hypoventilating or apneic patient, that the present invention demonstrates. Nor do they have any positive airseal mechanism to prevent leakage of gases and vapors during fiberoptic laryngoscopy/-bronchoscopy and tracheal intubation as has the present device.

The present invention is thinner than the above airways and is thus easier to insert into the oral cavity especially where jaw mobility is limited. In addition, the present invention has a better effective depth than the above airways, having a depth-adjustability range of more than 20mm from the highest to the lowest positions of the oral airway in reference to the oral mask. In exceptionally deep oral cavities some of the above airways had to be placed inside the lips in order to reach a functionally effective depth.

The present invention, because of its wide-body configuration, tends to stay better-positioned in the midline of the oral cavity then the above airways even in the complete absence of upper and lower teeth on one side of the mouth. This aids in directing the ET tube and/or the fiberoptic bronchoscope towards the glottis. It also keeps the tongue in a fixed anterior position so that it cannot impede visualization of the glottis by the fiberscope. A telescopic airway, developed years ago, had a rubber lip seal which, when positioned under the lips, could prevent leakage of anesthetic gases and vapors and assure adequate ventilation. In addition, it had a depth adjustability feature to adapt it to variable depth oral cavities. It did not, however, have a central channel large enough to pass a tracheal tube through.

The Blachly BITE BLOCK ASSEMBLY, ADAPTED FOR ADJUSTABLE MOUNTING AND HOLDING OF ORAL AIRWAYS, (U.S. Pat. Ser. No. 4,112,936) and the Blachly OROPHARYNGEAL AIRWAY AND BITE BLOCK ASSEMBLY AND METHOD FOR CLOSED PULMONARY VENTILATION (U.S. Pat. Ser. No. 4,270,531) provide gas seal and depth-adjustability features, but have no central channel for passage of a tracheal tube.

Several resuscitation devices were next examined. The BROOK AIRWAY, consisting of a combined airway and mask, could provide ventilation by the operator's expired air, but it was not depth-adjustable and had no central channel through which a tube could be passed. The Boehringer Resuscitator, likewise, depends upon the rescurer's expired air for ventilation. It, too, has no central channel for tube passage, and is not depth-adjustable.

Two other resuscitation devices were examined: The ELM MASK BREATHING SYSTEM (U.S. Pat. Ser. No. 4,449,526) and the DRYDEN TWO TUBE RESUSCITATION SYSTEM (U.S. Pat. Ser. No. 4,256,099.)

The ELAM device has an external, soft oral mask and nasal occlusion cushion which prevent oxygen leaking during ventilation. The device, however, does not provide for tracheal intubation or fiberoptic manipulation, since it does not provide a central channel large enough to accomodate a fiberoptic device and tracheal tube. It is, therefore, only a ventilating device for resuscitation purposes.

The DRYDEN device provides a separate two-channel airway which acts as a guide for two endotracheal tubes, one of which enters the esophagus and the other of which may or may not enter the trachea. A lip seal gasket and a nose clip prevent oxygen leakage during ventilation. The DRYDEN device is, therefore, both a ventilating and intubating device, but is designed primarily for resuscitation, to be an improvement on previous devices such as the ESOPHAGEAL OBTURATOR AIRWAY.

A further device, the PATIL/SYRACUSE ORAL AIRWAY AND MASK was next examined. It consists of a commercially available full size non-disposable face mask, modified by the addition of a fiberoptic port which can be covered by an attached cap when not in use. A specially-fabricated, non-disposable aluminum airway serves as a guide for a flexible fiberoptic scope after placement in the mouth. The mask covers the face, including the nose. Fiberoptic examination and/or endotracheal intubation is accomplished through the mask's fiberoptic port. No provision is made for esophageal occlusion.

None of the devices examined had all of the features incorporated in the present invention. It is felt, therefore, that this device is uniquely designed to accomplish all of its desired objectives, as well as to circumvent all the shortcomings of the above-mentioned devices.

The advent of the flexible fiberoptic bronchoscope (FFB) brought a new hope to those practitioners who are fortunate enough to enjoy the luxury of electricity. With this very effective tool it became possible to examine and intubate the trachea in a totally new way. Many difficult intubations were dealt with successfully. The problems however, although somewhat ameliorated, still remained. Secretions and/or blood in the oral cavity as well as edema, continued to plague the fiberoptic endoscopist as did inadequate oxygenation during attempts at endotracheal intubation since no device existed comparable to the present invention which could provide reliable ventilation as well as suction capabilities before and during tracheal intubation concurrent with the use of the flexible fiberoptic scope, especially in the hypoventilating or apneic patient.

Since fiberoptic endoscopy in the practice of anesthesiology is now accepted practice, it would appear that a breathing device which could ventilate a patient while increasing the effective capabilities of the fiberoptic scope, as well as making tracheal intubation easier to perform, and ultimately increasing the safety of the patient, would be the next logical step in the development of endotracheal anesthesia.

FIELD OF THE INVENTION

This invention in its various embodiments, relates to breathing devices, but more particularly to a device consisting of a ventilating oropharyngeal airway and an oral mask which when positioned together form an integral unit capable of adequately ventilating a patient either independent or concurrent with the performance of endotracheal intubation through the oral airway or through the nose, usually concomitant with the use of a flexible fiberoptic scope (FFS.).

The airway has a side arm which carries oxygen and anesthetic gases and vapors into the airway, and two lateral conduits which communicate with a main central channel by means of intercommunicating apertures. This arrangement aids in the proper distribution of gases and vapors throughout the airway, which, in turn conveys them to the orophaynx and hypopharynx, whence they ultimately reach the trachea. Waste carbon dioxide is removed in reverse order by the airway.

The airway also has a suction channel, independent of the airway central channel, which allows suctioning of the pharynx to be accomplished simultaneously with ventilation of the patient, with minimal or no interference in the transport of oxygen to the lungs.

A distensible port (UNIVERSAL ET TUBE CONNECTOR, DRYDEN), is positioned over the upper end of the airway's central channel housing (the airway neck) through which an endotracheal tube and/ or flexible fiberoptic scope is passed prior to intubation of the trachea. The port provides a positive airseal around the tube and/ or the fiberscope. Its design prevents its accidental dislodgement and herniation into the oral cavity as may occur with other devices having a fiberoptic port-bearing member mounted in a face mask (PATIL/SYRACUSE and Roger /Benumof modification thereof).

The oral mask has a rubber O-ring set into its upper surface. The O-ring has the same oblong shape as the upper segment of the airway. This provides a positive gas and vapor seal when the oral airway is passed into it. It also permits the airway to be adjusted upward or downward in the patient's oral cavity to adapt the unit more readily to the patient's anatomy. The mask is oblong in shape, having a semi-flexible, concave, peripheral lower surface which fits over and around the patient's mouth after the oral airway is in position in the mouth. An inflatable face cushion can be added to the under surface of the mask. This can be deflated or removed if extra airway depth is required.

Four headstrap attachment pins on the dorsal convex surface serve for headstrap attachment, thus holding the unit in snug apposition to the face contours, as well as stabilizing the airway in its appointed position.

An auxillary device, the BRONCHOSCOP-AIR (Dryden Corp.) is a fiberoptic bronchoscope adaptor which can accept a UNIVERSAL ET TUBE CONNECTOR over one or both ends of the device. A side-arm serves as a gas delivery limb. The lower end of the device may be affixed to a standard ET tube connector. The entire unit serves as a passageway for a fiberoptic bronchoscope or a suction catheter, as well as an ET tube, if desired.

A nose clip prevents loss of gases and vapors and helps to maintain the correct inspired oxygen concentration and adequate ventilation during orotracheal intubation and/or fiberoptic examination of the respiratory tract.

The primary object of the invention is twofold: FIRST, to provide a means whereby an endotracheal tube either singly or in concert with a flexible fiberoptic bronchoscope can be guided during the performance of fiberoptically assisted or 'blind' intubation of the trachea by either the oral or nasal route in the normal or in the 'DIFFICULT INTUBATION' patient, in the awake or unconscious (usually anesthetized) state, during spontaneous or mechanically (or manually) assisted or controlled ventilation.

SECONDLY, to provide a means whereby a patient can be effectively ventilated both before and during the performance of either oral or nasal, usually fiberoptically-assisted tracheal intubation, the objective being to prevent the onset of hypoxia and hypercapnia which may occur concurrently with difficult conventional or fiberoptic laryngoscopy, especially in the poor risk patient.

The device is thus designed to minimize and possibly eliminate the need for heroic measures such as retrograde intubation of the trachea, trans-laryngeal ventilation, cricothyrotomy, or emergency tracheotomy, any one of which may occasionally be necessary following failed intubation by conventional techniques.

The primary objective, therefore, is to make tracheal intubation easier and safer to perform. Many of the conditions associated with 'DIFFICULT INTUBATION' can be handled well by the judicious use of the present device.

Another objective is to eliminate the need for haste in the performance of tracheal intubation. With a steady state of oxygenation and control of ventilation assured throughout the procedure, haste, hassle, hypoxia and harm are minimized, and skill, safety, serenity and success are enhanced.

A further object of the invention is to prevent damage to the flexible fiberscope from the biting action of the patient's teeth which can occur if the fiberscope were to be passed unprotected through the mouth, especially in the awake uncooperative patient or in the anesthetized patient if relaxation should be inadequate and the anesthetic too 'light'.

Additionally the tip of the fiberscope is protected from secretions, at least during the initial stage of fiberoptic examination. Finally, the ET tube is protected against tube occlusion by the biting action of tee teeth which could lead to hypoxia due to a cutoff of oxygen supply to the lungs.

A further object is the prevention of dental injuries to the patient which frequently occur during the performance of difficult endotracheal intubation by standard techniques (i.e. routine laryngoscopy). The wide body of the airway provides a more sensible distribution of forces between airway and teeth than is possible with conventional narrow laryngoscope blades. Instead of pressure being applied to the upper incisors only, the airway provides a broader tooth contact surface and thus minimizes the possibility of damage to individual teeth.

An additional object is to prevent lip trauma which may occur when the upper lip is impinged between standard laryngoscope blades and the teeth.

A further object is to encourage the routine elective use of the device in place of routine laryngoscopy, the object being to prevent damage to the pharyngeal mucosa, epiglottis, vallecula and surrounding tissues, as well as damage to the vocal cords. Frequently, after difficult laryngoscopy, a bloody laryngoscope blade will be seen upon its removal from the mouth. The device is designed to eliminate the need for potentially harmful instruments to open and to expose the airways.

Another object is the elimination of the potential danger of tracheal laceration or perforation with potential, unwanted sequellae such as subcutaneous emphysema, infection, etc., which may occur following the use of stylets (particularly homemade ones), especially, in difficult conventional intubations. Rupture of the esophagus, likewise, may be prevented.

Another object is to eliminate the need for trans-tracheal injection of topical anesthetic, as well as bilateral superior laryngeal nerve blocks in preparation for modified 'awake' intubation. The device is inserted into the topically anesthetized oral cavity, following which the vocal cords are visualized with the fiberscope. The vocal cords and trachea are then sprayed with a topical anesthetic through the FFS. A sleep dose of fast-acting intravenous anesthetic, followed by a paralyzing dose of a muscle relaxant (such as succinylcholine) are given. The FFS is passed into the trachea followed by the ET tube. The potential danger of neck infection from the trans-tracheal injection is thereby eliminated.

A further object is an airway design which minimizes potential damage to the pharyngeal mucous membranes. The gently contoured posterior surface of the airway's pharyngeal segment allows a less traumatic placement in the oropharynx compared with other intubating airways whose more sharply round posterior surfaces cause the tip of the airways to be potentially more traumatic to the pharyngeal mucosa upon insertion. In addition, the gently rounded surface of the present device more accurately conforms to the anatomic configuration of the oropharynx — an important consideration if the airway is left in place for a considerable length of time, since contact of the airway with the sensitive mucous membranes is not concentrated on a narrow zone. Potential pressure necrosis of mucosal tissue is hopefully prevented.

An additional object of the invention is to provide a teaching tool for the training of anesthesiologists, nurse anesthetists, and medical and veterinary students in the techniques of flexible fiberoptic laryngoscopy and bronchoscopy, as well as tracheal intubation under controlled conditions. The patient can be ventilated as long as the student needs to practice. There is no need for haste, and no excuse for hypoxia. The patients can be conscious and breathing spontaneously OR they can be anesthestized and spontaneously breathing, OR they can be anesthestized and paralyzed by a muscle relaxant.

A corollary to the above is the potential use of the device in the study of laryngeal anatomy and function by the physiologist, anatomist, laryngologist, voice teacher, etc. in awake volunteers under topical anesthesia.

A further object is to provide a ventilating, intubating airway through which the patients vocal cords and the function thereof can be routinely examined fiberoptically at the completion of operations such as thyroidectomy and radical neck dissection without the necessity of repeat conventional laryngoscopy with its attendant hazards to the teeth under 'light' anesthesia (upon emergence from anesthesia). There is no need to force the mouth open with the laryngoscope, while the patient is 'light' and poorly relaxed (after reversal of muscle relaxant) OR when recovering from inhalation anesthestic agents. With the airway already in place, one needs merely to make the necessary assessment with the fiberoptic scope while the patient bites down on the wide plastic airway, NOT a narrow metal laryngoscope. If damage to the recurrent laryngeal nerve IS suspected and re-exploration of the operative field is decided upon, the airway is already in place and the anesthetic can easily be resumed.

Another object: To enable pre-operative fiberoptic examination to be made, immediately BEFORE thyroidectomy, radical neck dissection, etc. to check on vocal cord function, position and configuration. The patient to be anesthetized, spontaneously breathing through the airway, not paralyzed, with intubation to follow after the examination is completed.

Coincidental with the above is the need to provide a ventilating airway through which the patient's vocal cords and surrounding structures, and the function thereof can be examined fiberoptically under 'light' general anesthesia with spontaneous respiration in cases of alleged dysfunction, to rule out (or in) alleged damage from previous surgery (such as thyroidectomy), tracheal intubation, trauma from accidents, or in cases of psychogenic dysphonia. Some are potential litigation cases. Intubation is avoided. Teeth injuries, which may occur during routine laryngoscopy under 'light' anesthesia are avoided. The nasal route for examination, with its potential complications, are avoided. These include:
  a. Bacteremia.
  b. Inflammation or ulceration of nose.
  c. Painful nose.
  d. Stuffy or runny nose post-operatively.
  e. Blood clot coughed out from nose post-operatively.
  f. Sinusitis.
  g. Perforation and dissection of posterior pharyngeal wall creating a false passage and a potentially serious infection.
  h. Dislodgement of tonsil tissue and passage into trachea.
  i. Nasal hemorrhage.

Another object of the device is to assure ventilation of the anesthetized patient at the same time that preparation of the nasal passages is, being made prior to naso-tracheal fiberoptic examination and naso-tracheal intubation. The nasal passages can be cocainized or sprayed with a topical anesthetic. Then the nose clip is reapplied, with minimal leakage of anesthetic gases and vapors before the actual procedure begins.

The device also allows free access to the nose for insertion of a naso-gastric tube, esophageal stethoscope or suction catheter at the same time that the patient is being ventilated by the device.

An additional object: To provide better conditions for the performance of Diagnostic Fiberoptic Bronchoscopy under general anesthesia with or without tracheal intubation, the object being to prevent air trapping and hypoventilation which may occur when the interior cross-sectional area of the ET tube (with cuff inflated) is compromised by the presence of an indwelling fiberscope.

Another object: To provide an airway which can serve as a guide for a flexible fiberoptic bronchoscope and which can assure adequate ventilation of a patient before, during and after the performance of bedside bronchofiberoscopy via either the oral or nasal route, especially in the poor-risk patient. The airway acts as a bite block, and it prevents the tongue from interfering with the fiberscope by keeping it in a central, anterior position in the oral cavity.

A further object of the present invention is to provide a means whereby secretions can be aspirated from the hypopharynx in a non-intubated patient under general anesthesia without interruption of ventilation. Simple aspiration with a suction catheter can be accomplished through the airway's suction channel or through the airway channel with minimal interference with delivery of oxygen to the patient.

With a patient under general anesthesia, previously intubated with the aid of the present device, it is possible to perform suctioning of the tracheobronchial tree through the ET tube without interruption of ventilation. The ET tube is temporarily disconnected from the breathing circuit, its cuff deflated, and its upper end covered with a fiberoptic bronchoscope adaptor. Ventilation is effected by means of the airway around rather than through the ET tube. Hypoventilation with dangerously low oxygen levels in the lungs is prevented.

In the case of an awake, non-intubated patient needing trachobronchial toilet (TBT) by means of the flexible fiberoptic bronchoscope, the ventilating airway can provide effective ventilation before, during and after the procedure.

In each of the above situations, more effective ventilation is possible than with traditional techniques, and hypoxic episodes, especially in the poor-risk patient, are hopefully avoided.

The device would be useful for training in 'blind' nasotracheal intubation techniques.

(1) Ventilation is spontaneous throughout the procedure.

(2) The ventilating airway is used to supply oxygen to the patient both between and during intubation attempts with the respirations assisted, if necessary, between attempts.

(3) The airway is raised up off of the posterior pharyngeal wall to provide space for passage of the nasotracheal tube.

(4) May be used in conjunction with the PATIL INTUBATION GUIDE-AUDIBLE or the BAAM device 'BEACK AIRWAY AIRFLOW MONITOR'.

(5) If desired, an assistant can monitor the procedure orally through a flexible fiberscope passed through the airway.

A further object: To provide a device which can render effective ventilation, and assist in orotracheal or nasotracheal tube placement in the critical care setting (e.g. patients with Guillain-Barré syndrome, Myasthenia gravis, etc.). Also, to assist in nasotracheal tube change in the Intensive Care Unit (I.C.U.), for example, especially in the difficult-to-intubate patient, or in the poor-risk patient.

Another object of the present device is to assist in retrograde intubation of the trachea in cases of failed intubation. The airway can fulfill its ventilating function at the same time that a guide wire (or catheter) is threaded up through the glottis into the pharynx. A biopsy forceps, passed through a flexible fiberscope, can then be used to pull the guide wire up through the airway central channel, following which an ET tube is passed downward over the guide wire into the trachea, either through the airway or after airway removal over the guide wire.

Alternatively, a forceps passed through a nasally-placed fiberscope can pull the guide wire out through the nose if a nasal placement of the ET tube is desired.

A futher object is to be able to cope with the problems of an indwelling naso-gastric tube or with bilateral nasal obstruction preexisting prior to the anesthetic induction, both of which can make it difficult to ventilate the patient before intubation, if a standard full-sized mask is used. The present device solves both problems.

An additional object is to provide a ventilating airway for surgery performed on the nose (e.g., submucous resection, rhinoplasty, reconstructive surgery) and contiguous structures (such as the maxillary sinuses) which can be inserted at the end of the operation, after tracheal extubation, while the patient is still fairly deeply anesthetized, or before reversal of the muscle relaxant, and then removed when adequate respirations are resumed, but before coughing efforts occur. The oral mask makes it possible to ventilate the patient until return of spontaneous respiration while avoiding contact, either directly or indirectly, with any of the structures which have been operated upon. There are no problems with mask fit and ventilation such as frequently occur when a full-size face mask is applied over operative dressings in the presence of obstructed nasal passages.

In line with the above is the need to provide a ventilating airway for opthalmic surgery which can be inserted either at the start of the anesthetic before tracheal intubation, or at the end of the operation, after tracheal extubation, while the patient is still fairly deeply anesthetized, or before reversal of the muscle relaxant and then removed when adequate respirations are resumed. but before coughing efforts occur. Th oral mask makes it possible to ventilate the patient until return of spontaneous respiration while avoiding any contact with or displacement of the ophthalmic shield (or eye bandage); thus no possible pressure can be exerted on the eyeballs, as may occur with an ordinary full-size face mask. There is, therefore, no possibility of damage to the operated eye (or the normal one) from mask pressure, and oculocardiac reflexes are avoided. Increased intraocular pressure, which may occur when the patient reacts with the ET tube still in place, and which results from 'bucking' on the tube, is completely avoided. The surgeons are happy and all is well. In addition, ventilation is much easier to accomplish with the present device since there is no problem with mask fit such as frequently occurs when a full-size face mask is applied over an eyeshield.

A further object is the use of the device to aid in 'awake' intubation in a variety of situations: (1) In conscious, poor-risk patients in whom adequate oxygenation is a 'must' (e.g. coronary bypass; 'crash' induction of general anesthesia is avoided, and deleterious effects of 'deep' anesthesia are avoided); (2) In extreme obesity; (3) In emergency operations on patients having full stomachs and obstetrical delivery patients having full stomachs under general anesthesia, the object being to prevent regurgitation with its potentially serious, even lethal, complications; These include:

(a) Fatal maternal asphyxia and possible fetal death.
(b) Hypoxic brain damage of fetus or mother.
(c) Mendelsohn's syndrome (aspiration pneumonitis).
(d) Lung abscess.

The Sellick maneuver (cricoid pressure) is recommended in conjunction with the above.

(4) 'Awake' intubation is used also, for patients who are to have cervical spinal cord procedures (e.g. cervical spinal cord decompression) with intubation performed before the induction of general anesthesia, and after the immediate post-intubation assessment of neurological function by the neurosurgeon, the purpose being to avoid damage to the spinal cord which may occur from motion of the head and neck during routine laryngoscopy under general anesthesia.

(5) And for patients having cervical spine abnormalities with severe limitation of head and neck ability, who may be deemed too risky to anesthetize before conventional intubation attempts under general anesthesia.

(6) 'Awake' intubation is also used for patients undergoing laryngectomy or radical neck dissection with elective tracheotomy to be performed before the start of the procedure. The device may be removed upon completion of the tracheotomy. Likewise, 'awake' intubation may be used during the performance of tracheotomy itself (either emergency or elective) with the device removed at the end of the procedure. In addition, it can be used during and after the placement of tracheostomy tubes to assist in fiberotpic verification of their correct positionings.

The device provides effective ventilation as needed in each of the above situations.

Another object is to provide a means whereby a slow, careful induction of general anesthesia can be provided for poor-risk surgical patients. Routine laryngoscopy is avoided. Release of stress hormones and their deleterious effects (tachycardia, arrythmias, elevation of blood pressure, etc.) are hopefully avoided. The oral cavity and tongue are anesthetized with topical anesthetic before the airway is inserted, and before anesthetic induction is begun. Anesthetic agents are carefully titrated Oxygen is given both before and after placement of the airway. Fiberoptic intubation is accomplished while the patient is being ventilated.

An additional object: To provide a device which may be useful in Neodymium-YAG (Nd-YAG) laser resection of major airway obstructing tumors, as well as laser surgery of the larynx. Correct use of the ventilating airway could eliminate the need for subglottic jet ventilation, and could eliminate barotrauma which may result from the subglottic technique. In addition, the use of high frequency positive pressure ventilation (HFPPV) might be eliminated. Hypoventilation and hypercarbia may be better managed with the ventilating airway.

A further object of the invention is to minimize leakage of nitrous oxide and anesthetic vapors into the operating room during tracheal intubation, thus contributing to pollution control.

A corollary to the above: To provide a device which will allow the application of topical anesthetics to the pharynx, glottis and trachea through the FFS in a completely closed system. This eliminates the need for preliminary laryngoscopy and direct topical anesthetic spraying in the 'difficult intubation' patient.

Another object: To provide a device which can help to avoid repeat doses of succinylcholine during difficult routine intubation attempts. Frequently, the induction dose wears off and more has to be given. Repeat doses may cause severe bradycardia (slow pulse) or asystole (absence of pulse or cardiac arrest) unless preceeded by adequate doses of an anti-cholinergic agent (such as glycopyrrolate). With the airway already in place, the patient can be switched to an inhalation agent (such as isoflurane) with fiberoptic manipulation and intubation to follow. Succinylcholine should be completely avoided if there is a pre-existant condition which may predispose to the development of hyperkalemia.

A further object: To provide a device which can lessen the chances of inadvertent esophageal intubation. Under the optimal ventilating and intubating conditions provided by the device, a thorough and unhurried determination of the ET tube's position can be made with the FFS, and a potential tragedy averted.

A further object is to provide a device which would be helpful to personnel with physical disabilities of various types including recent acromioclavicular or sternoclavicular separations; rotator cuff injury; recent fractures of wrist, forearm, fingers; arthritis of the shoulder joint; fractured clavicle; muscular weakness of the arm or shoulder (e.g. tennis elbow); brachial plexus palsy, etc.) any one of which may severely limit the ability to exert the strong upward force that is needed in the performance of routine laryngoscopy, especially in the difficult intubation. In addition, the increasing number of females entering the specialty of anesthesiology and nurse anesthesia makes a strong case for a device which can help those with weaker musculature to function well in their chosen field.

An additional object is to minimize the health hazard to the anesthesiologist which may occur when fingers placed in the patient's mouth are exposed to hepatitis, herpes simplex, and Human T-cell lymphotropic virus Type III (TTLV III), and other pathogens. There is no need to insert fingers when the fiberoptic airway is used, ad no need to insert a bite block, packing, or an oral airway next to the ET tube after tracheal intubation.

A further object is to provide a device which can cope with unusual facial configurations (such as acromegaly, gigantism, rhinophyma, etc.) in case endotracheal intubation is considered unnecessary (e.g. minor surgery, short procedures). These faces are frequently difficult to fit with ordinary full-size face masks in order to provide a leakproof system.

A further object is to provide a ventilating airway a variation of which, if made of resilient, non-toxic material, (such as polyurethane) can serve as a bite block during electroconvulsive therapy, and which can effectively oxygenate the patient both before and after the shock(s), and which has less infection potential to the operator than standard bite blocks in current use.

A further object is to provide a useful device for emergency ventilation of the unconscious patient during CPR (Cardio-Pulmonary Resuscitation).

A. Areas where device could be used:
 (1) In the hospital (emergency room, special procedure rooms, etc.).
 (2) In medical and dental offices, nursing homes, etc.
 (3) Schools, hotels, theaters, sports arenas, factories, office buildings, stores, commercial aircraft, ocean liners, ambulances, etc.
 (4) In the military.

Any place having large concentrations of people should have adequate rescue breathing equipment on hand to handle emergencies.

B. The ventilating airway, with or without a bacterial filter, can function as a RESCUE BREATHING DEVICE and 'buy' valuable time before the arrival of more experienced personnel (first department paramedics, anesthesiologists, etc.).

C. Even without the passage of an endotracheal tube 'blindly' by the inexperienced operator, the device may prevent hypoxic brain damage and/or death, if used properly and expeditiously.

The ultimate objective of the invention is improvement in the standard of patient care. The correct use of the device could lead to:
 (a) a lessening in the number of injuries to the lips and teeth, as well as the nasal, pharyngeal, laryngeal and tracheal and esophageal tissues;
 (b) prevention of hypoxia-initiated brain damage and/or death from unrecognized esophageal intubation, or, from 'failed' intubation;
 (c) prevention of hypoxia and hypercarbia-initiated deleterious cardiac arrthythmias and the ever-present possibility of cardiac arrest, and, finally,
 (d) a diminution in the number of lawsuits referable to the above.

Since the use of the flexible fiberoptic bronchoscope is now accepted technique in the practice of anesthesiology, it would appear that practitioners are now duty-bound to become proficient in the use of the device.

In the legal realm it would appear that a practitioner might be judged guilty of malpractice if he or she were unable to use the FFS properly in the clinical setting, or if he or she failed to use the device when clearly indicated.

Since the present invention is, to my knowledge, the only device specifically designed to accomplish all of the above-mentioned objectives I believe that it will be a very valuable addition to the armamentarium of the clinician, and will serve to encourage the more frequent use of the flexible fiberoptic bronchoscope with resultant advantages to everyone.

Practice with the device and with the fiberoptic scope on consenting patients on a regular basis will give much-needed experience to the clinician so that he or she will be ready to function effectively when the difficult intubation or other special situations make their appearance, and the chances of a successful outcome will be greatly enhanced.

When the device is thought of first instead of last (after all other measures have failed), and when it is used electively, instead of as a last resort, is when its true potential will be realized.

It is the belief of the designer that the ventilating, intubating airway may very well establish a new and better standard of patient care. Older intubation techniques may ultimately be judged against the fiberoptic-facilitating, depth-adjustable, ventilating and intubating airway/mask device.

THE DRAWINGS

In the drawings:

FIGS. 3–7 are views of an oral mask wherein FIG. 3 is a front elevational view of an oral mask;

FIG. 4 is a rear elevational view of the oral mask;

FIG. 5 is a side elevational view of the oral mask and it is to be understood that the other side in an elevational view appears the same as in FIG. 5;

FIG. 6 is a bottom plan view of the oral mask;

FIG. 7 is a top plan view of the oral mask;

FIGS. 8–13 are views of an oral airway wherein FIG. 8 is a rear elevational view;

FIG. 9 is a side elevational view from the right;

FIG. 10 is a side elevational view from the left;

FIG. 11 is a top plan view;

FIG. 12 is a front elevational view;

FIG. 13 is a bottom plan view;

FIGS. 14–19 illustrate the combination of the oral mask and the oral airway wherein FIG. 14 is a front elevational view of the oral airway and the outlet of the oral airway is illustrated;

FIG. 15 is a rear view of the oral airway and the outlet of the oral airway is not illustrated;

FIG. 16 is a side elevational view of the combination from the left side;

FIG. 17 is a side elevational view of the combination from the right side;

FIG. 18 is a top plan view of the combination;

FIG. 19 is a bottom plan view of the combination;

FIGS. 24 and 25 are of a Universal ET tube connector wherein FIG. 24 is a bottom plan view;

FIG. 25 is a side elevational view;

FIGS. 26, 27 and 28 are of a plug and cap unit wherein FIG. 26 is a bottom plan view;

FIG. 27 is a top plan view;

FIG. 28 is a side elevational view;

FIG. 30 is a side elevational view of the combination of the ET tube connector and the plug and cap unit with the stem of the plug and cap unit in the ET tube connector and the ET tube connector and the plug and cap unit are positioned close to each other;

FIGS. 31, 32 and 33 are for another species of an oral airway wherein FIG. 31 is a front elevational view of the oral airway;

FIG. 32 is a side elevational view of the oral airway with the side views, from either side, being the same;

FIG. 33 is a rear elevational view;

FIGS. 37–39 are views of a modified clear plastic face mask wherein FIG. 37 is a side elevational view of the modified clear plastic mask with an oral airway positioned in the face mask;

FIG. 38 is a top plan view of the modified clear plastic face mask with part of the oral airway in cross-section;

FIG. 39 is a bottom plan view of the modified clear plastic face mask and illustrates the oral airway positioned in the face mask;

FIGS. 40–47 are for another species of an oral airway which has a removable spline wherein FIG. 40 is a side elevational view of the left side of the oral airway;

FIG. 41 is a front elevational view of the oral airway positioned in an oral mask illustrated in phantom;

FIG. 42 is a rear elevational view of the oral airway;

FIG. 43 is a top plan view of the oral airway minus the removable spline;

FIG. 44 is a top plan view of the oral airway with the spline in position;

Figure 40:
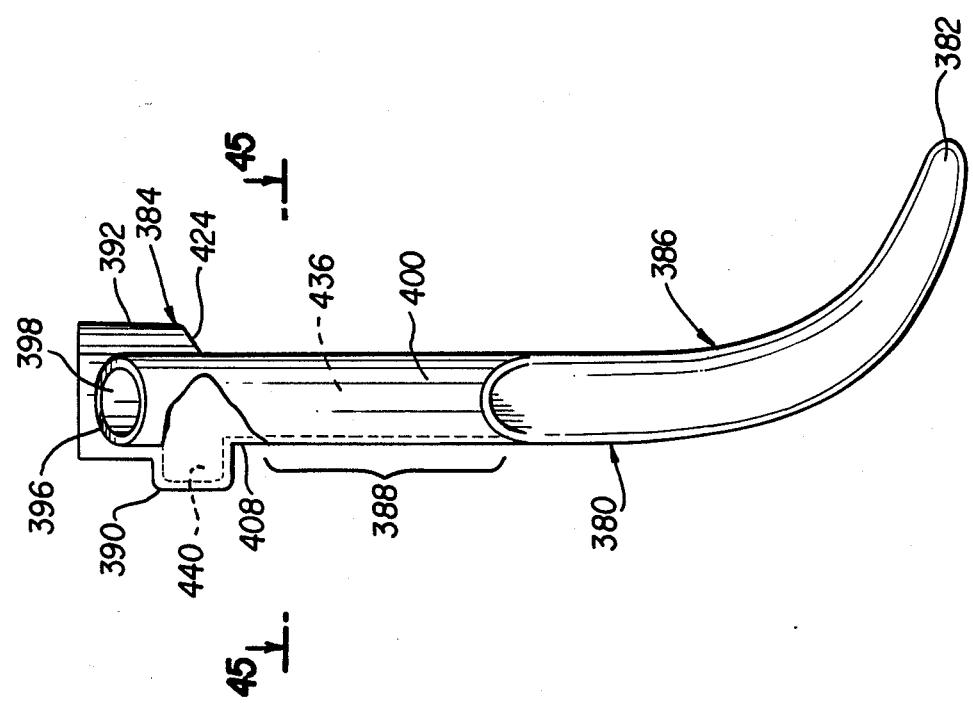
Figures 48, 49, 50, 51, 52, 53:
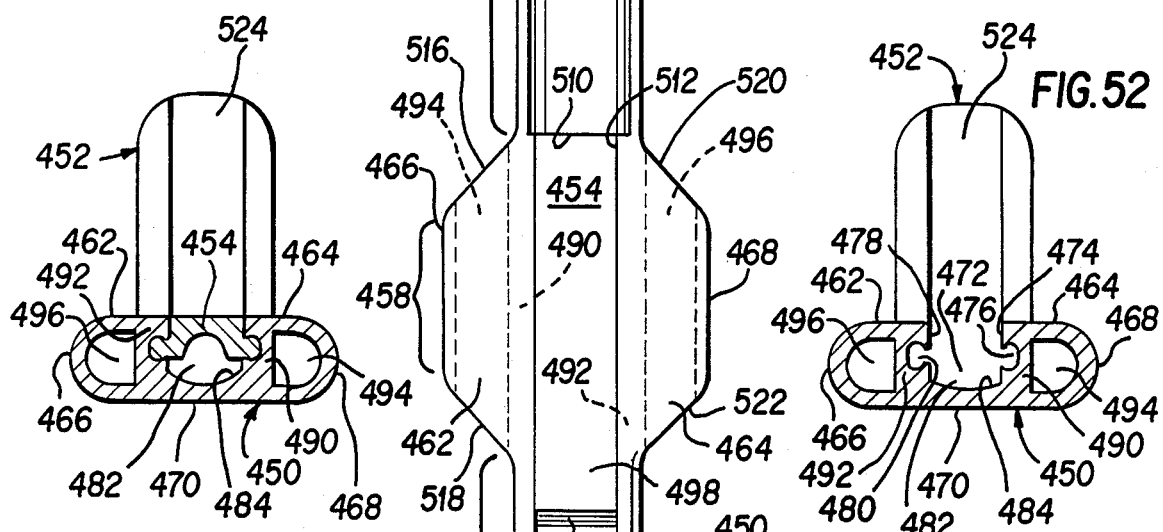

FIG. 45, taken on line 45—45 of FIG. 40, is a cross-sectional view of the oral airway in the dental contact zone with the spline in position;

FIG. 46 is a cross-sectional view of the oral airway in the dental contact zone minus the removable spline;

FIG. 47 is a side elevational view of the removable spline;

FIGS. 48–56 are for a take-apart airway similar to the airway illustrated in FIGS. 31–36 wherein FIG. 48 is a front elevational view of the airway;

FIG. 49 is a lateral cross-sectional view taken on line 49—49 of FIG. 48 with the spline positioned in the neck of the airway.

Figure 22:
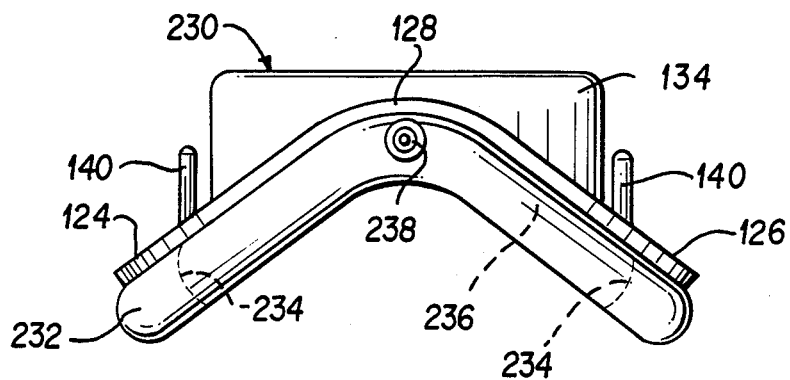
FIG. 22 is a bottom plan view of another species of the oral mask incorporating an inflatable face cushion to place between the body of the mask and the individual.
Figure 23:
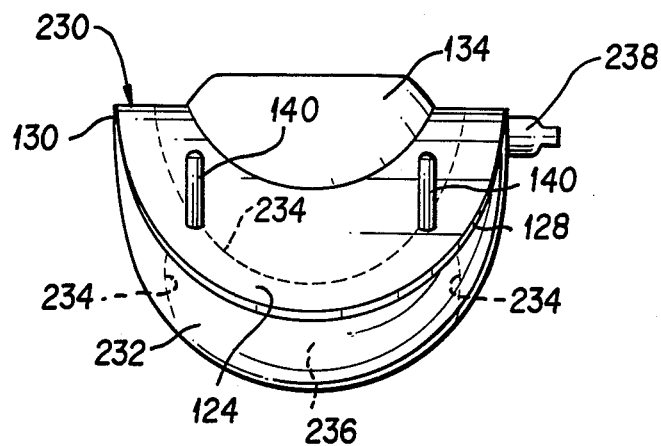
FIG. 23 is a side elevational view of the oral mask and inflatable face cushion combination of FIG. 22.
Figure 55:
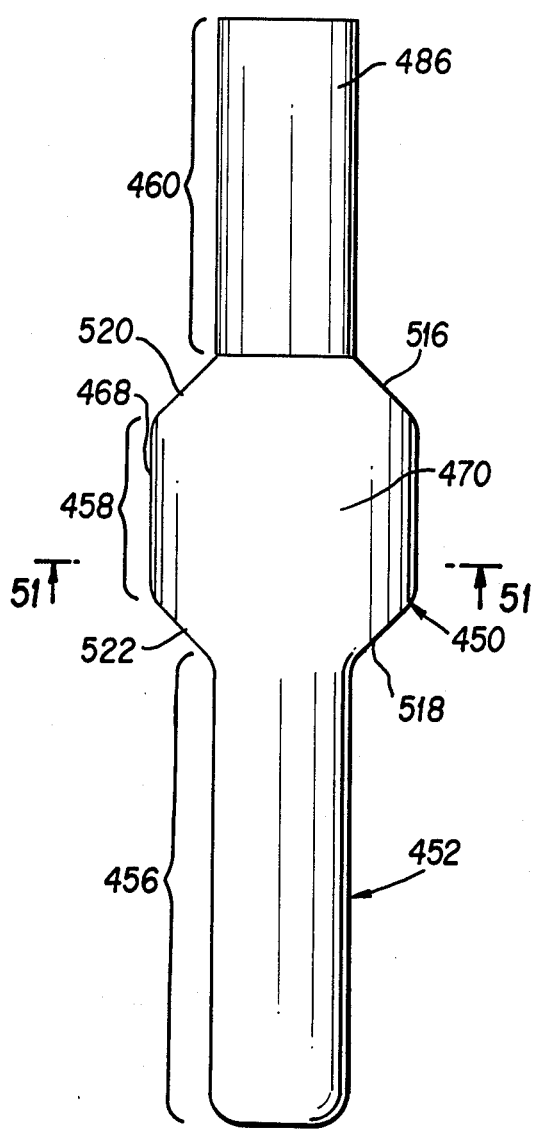
Figure 54:
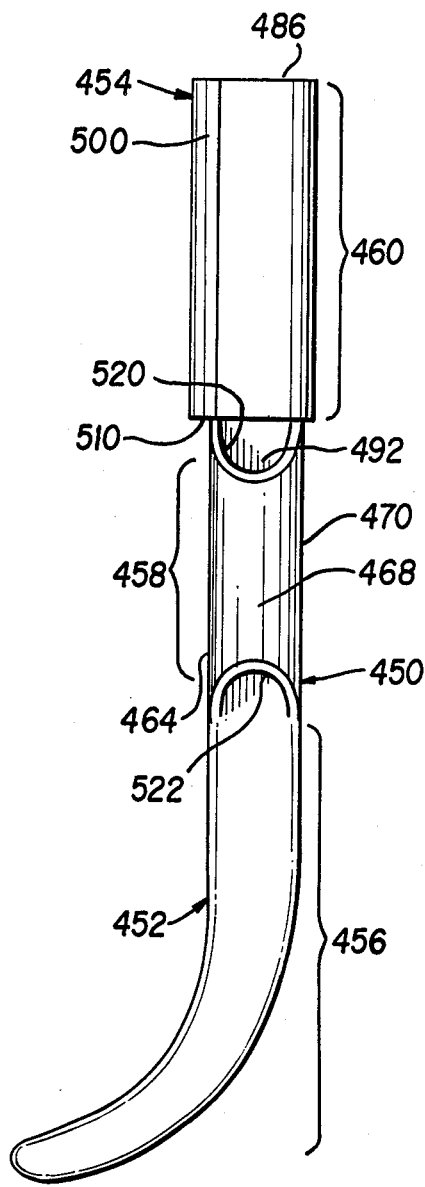
Figure 56:
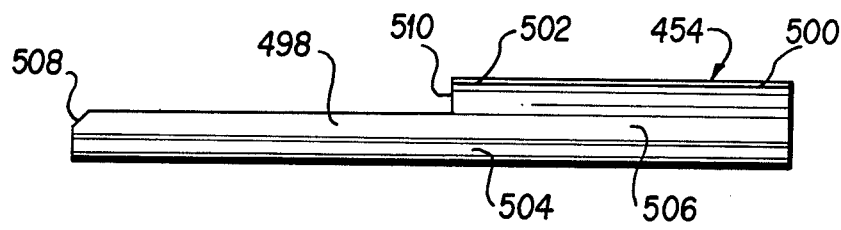
Figures 57, 58, 59:
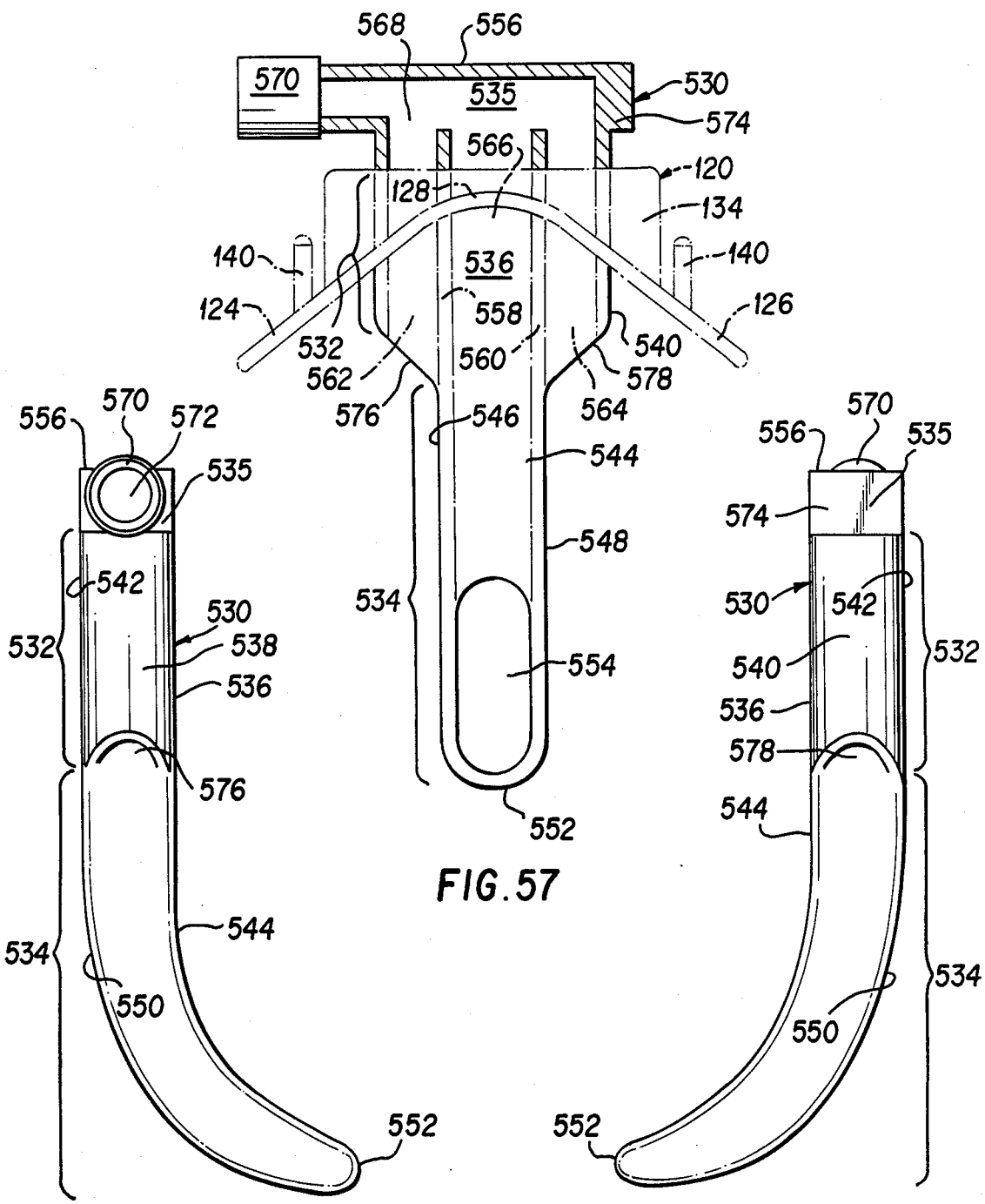
Figure 60:
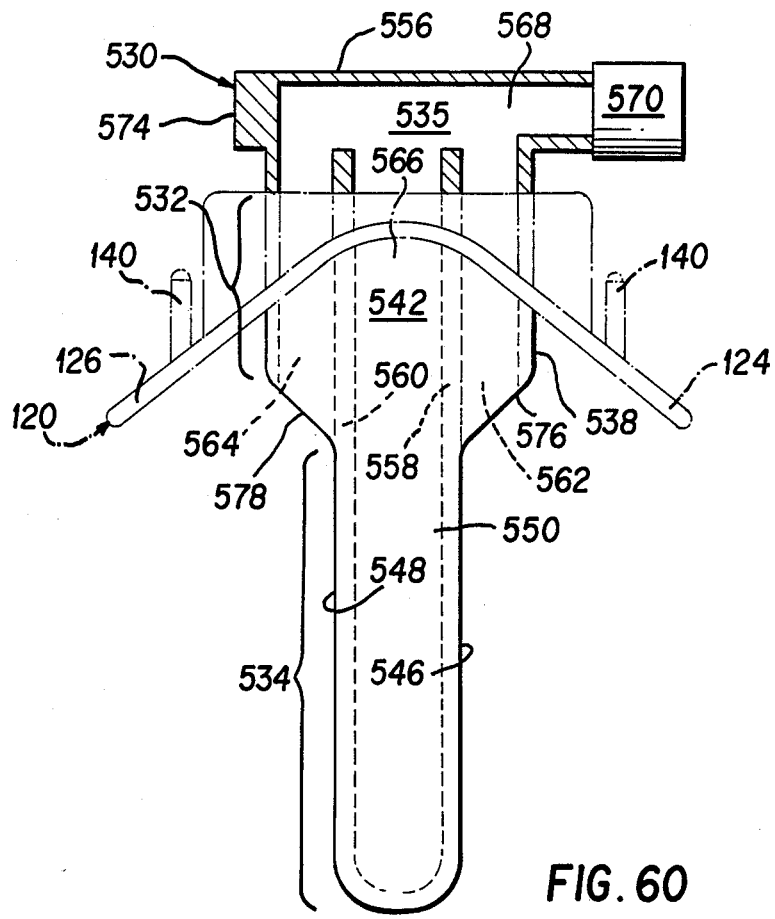
Figure 61:
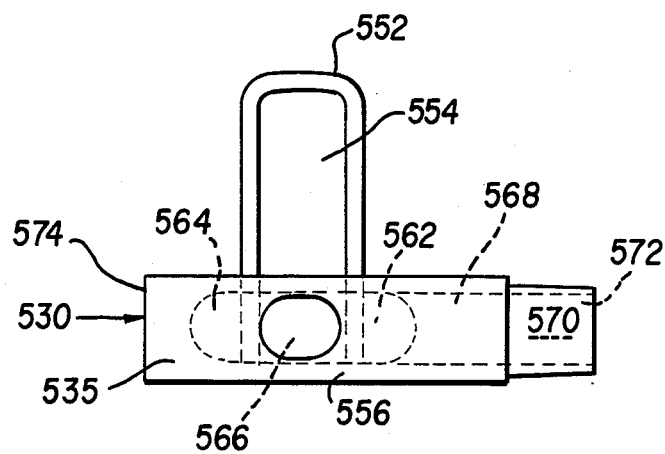
Figure 62:
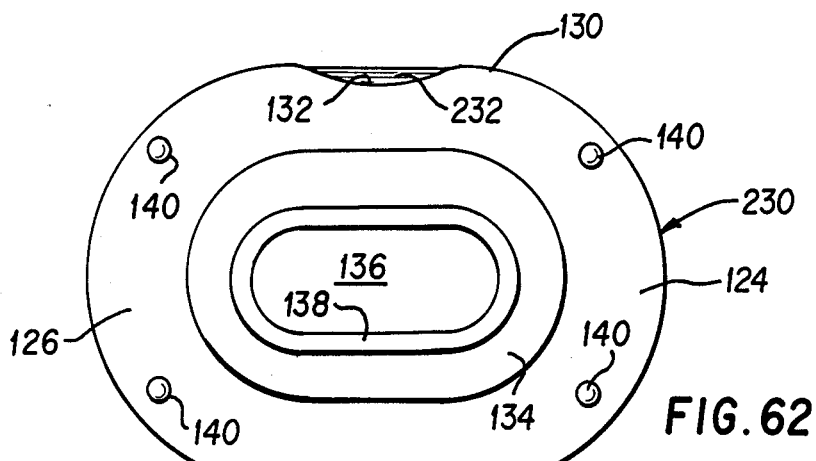
Figure 63:
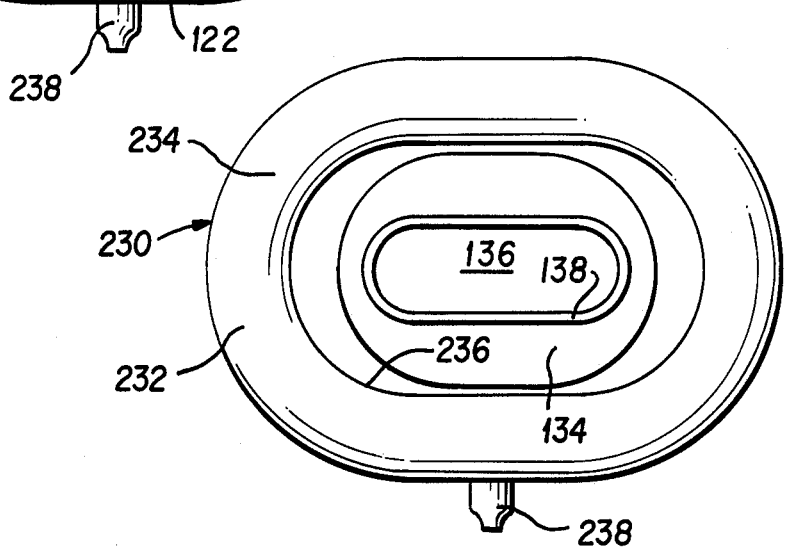
Figure 64:
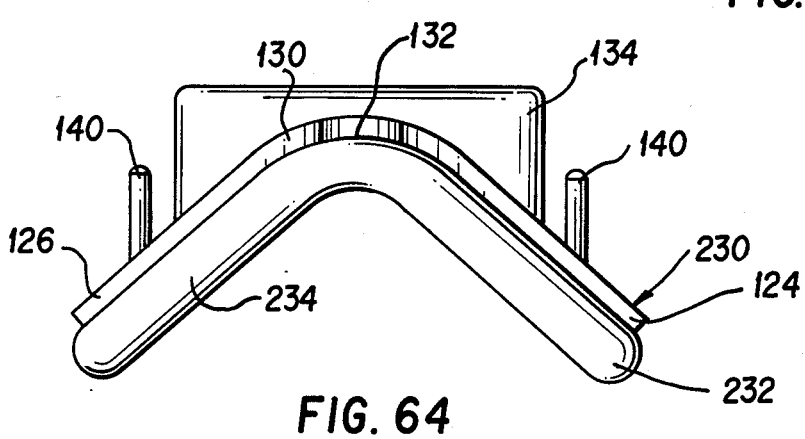
Figure 65:
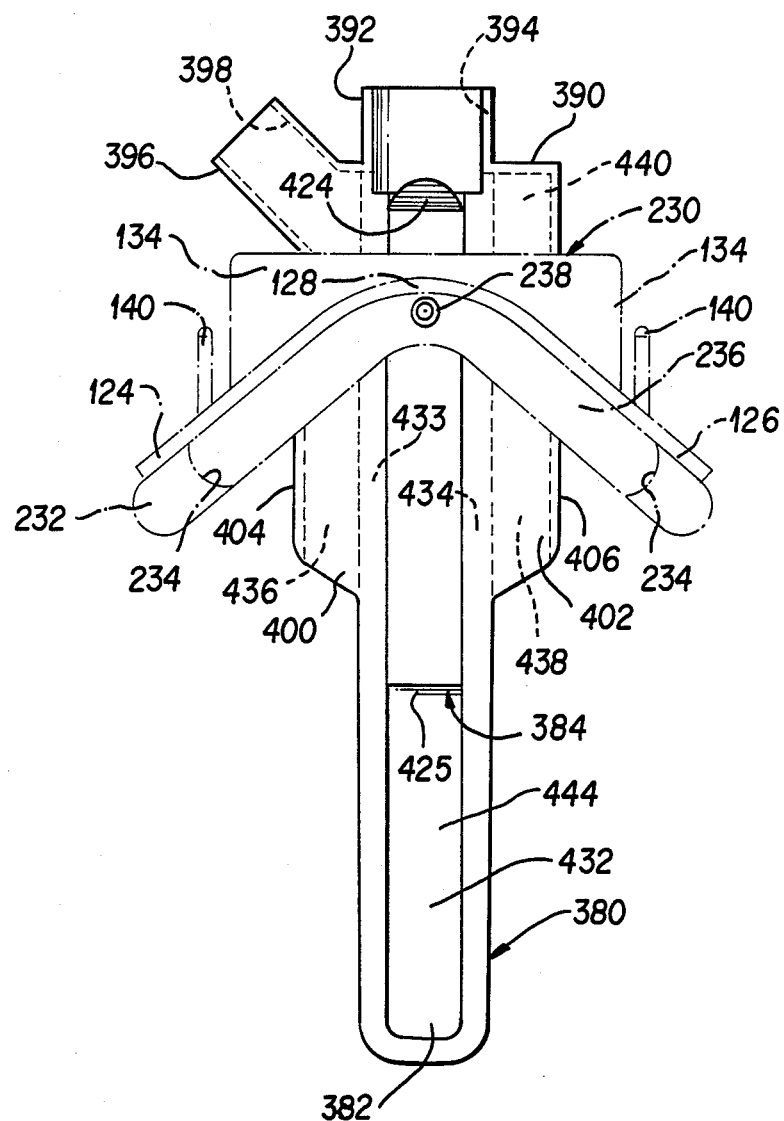

FIG. 50 is a cross-sectional view of the airway restricted to the neck with the spline removed from the neck of the airway;

FIG. 51 is a lateral cross-sectional view taken on lines 51—51 of FIG. 55 of the dental contact area of the airway with the spline in position;

FIG. 52 is a lateral cross-sectional view of the dental contact area of the airway without the spline;

FIG. 53 is a bottom plan view of the airway;

FIG. 54 is a right side elevational view of the oral airway;

FIG. 55 is a rear elevational view of the oral airway;

FIG. 56 is a side elevational view of the spline;

FIG. 57 illustrates a depth adjustable, non-intubating, non-fiberoptic oral airway wherein FIG. 57 is a front elevational view, with the gas commonality housing in section, and with an oral mask in phantom positioned on the oral airway;

FIG. 58 is a left side elevational view of the oral airway;

FIG. 59 is a right side elevational view of the oral airway;

FIG. 60 is a rear elevational view of the combination of the oral airway and oral mask with the oral mask in phantom;

FIG. 61 is a top plan view of the oral airway;

FIGS. 62, 63 and 64 are views of the oral mask and the inflatable cushion of FIGS. 22 and 23 wherein FIG. 62 is a front elevational view;

FIG. 63 is a rear elevational view;

FIG. 64 is a top plan view; and,

FIG. 65 is a front elevational view of a combination of the oral airway of FIGS. 40–47 and oral mask of FIGS. 22, 23 and 62–64.

THE SPECIFIC DESCRIPTION OF THE INVENTION

Figure 1:
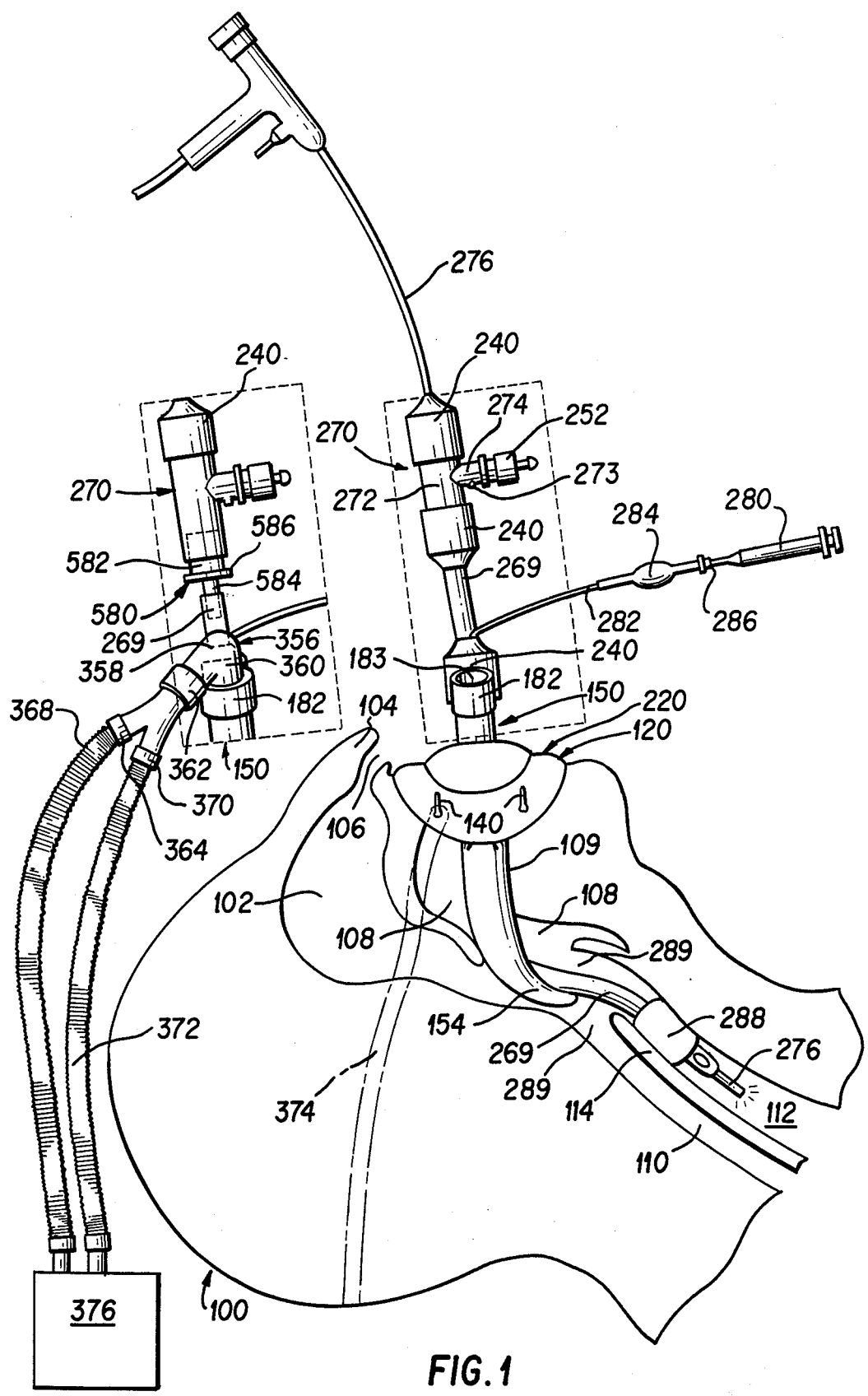
FIG. 1 is a fragmentary longitudinal cross-sectional view of the head of an individual illustrating the nasal cavity, the oral cavity, the esophagus and the trachea with an oral mask positioned over the mouth and the peri-oral tissues of the individual and with the oral airway in the oral mask and within the oral cavity.
Figure 2:
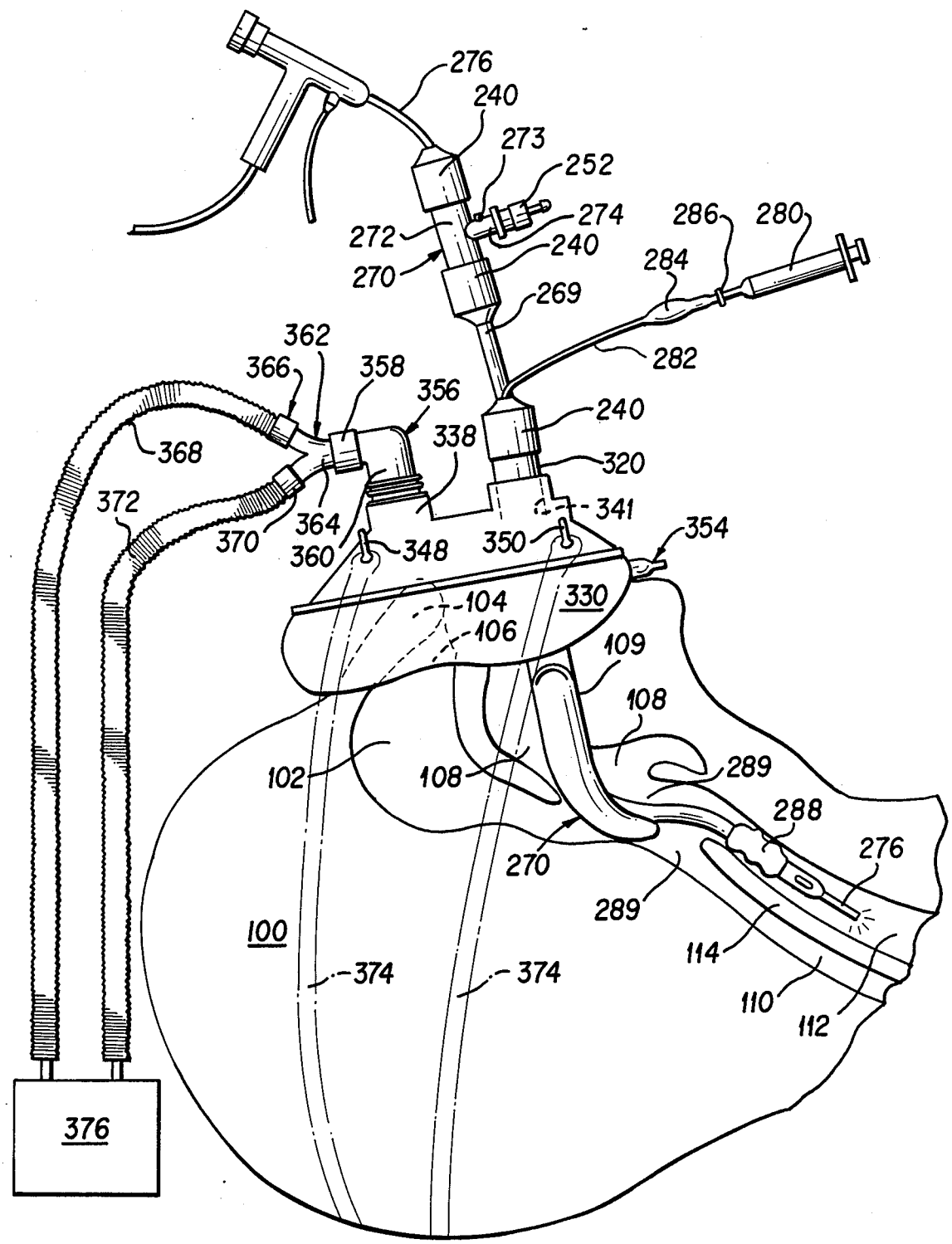
FIG. 2 is a fragmentary longitudinal cross-sectional view of the individual illustrating the nasal cavity, the oral cavity, the esophagus and the trachea and a full face mask overlying the nose, the mouth and peri-oral tissues of the individual and with the oral airway in the full face mask and within the oral cavity.

In FIGS. 1 and 2 there is illustrated in cross-section the head 100 of a human being. In the head 100 there is a nasal cavity 102, a nose 104 and a nostril 106 connecting with the nasal cavity 102.

There is an oral cavity 108. At the right of the oral cavity 108 there is an esophagus 110. The esophagus 110 leads to the stomach of the individual. Above the esophagus 110 there is a trachea 112. The trachea leads to the lungs of the individual.

A tissue 114 separates the esophagus 110 from the trachea 112.

In many operations under general anesthesia one of the objectives is to position an endotracheal tube in the trachea of the individual. Under certain conditions this is accomplished with the aid of fiberoptic guidance.

Many of the problems encountered in the positioning of the endotracheal tube in the trachea have been presented in the foregoing part of this patent application, see THE BACKGROUND OF THE INVENTION. There arise situations before and during the placing of the endotracheal tube into the trachea which can be alleviated by judicious use of the inventions disclosed in the patent application. A main reason for the inventions of this patent application is to try and make it possible to successfully place the endotracheal tube into the trachea under difficult intubating conditions and to avoid hypoxia and hypercarbia. There are other useful ancillary uses for the inventions of this patent application. The various species of the invention give considerable latitude to the anesthesiologists to cope with the problems which arise under various ventilating and intubating conditions.

Figure 6:
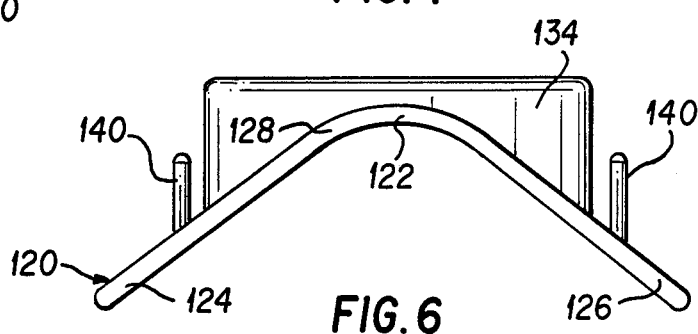
Figure 7:
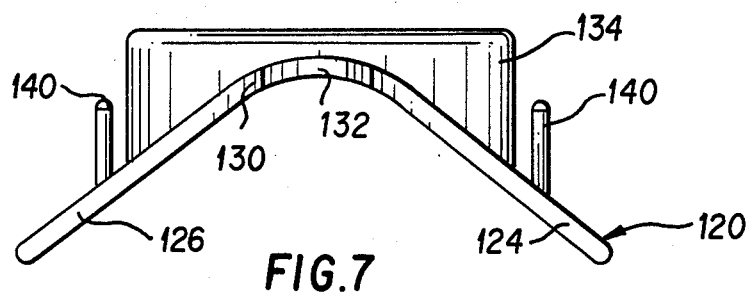

In FIGS. 3–7 there is illustrated the oral mask 120. In FIGS. 6 and 7 it is seen that the oral mask is curved and has a central part 122 and the side 124 and a side 126.

Figure 3:
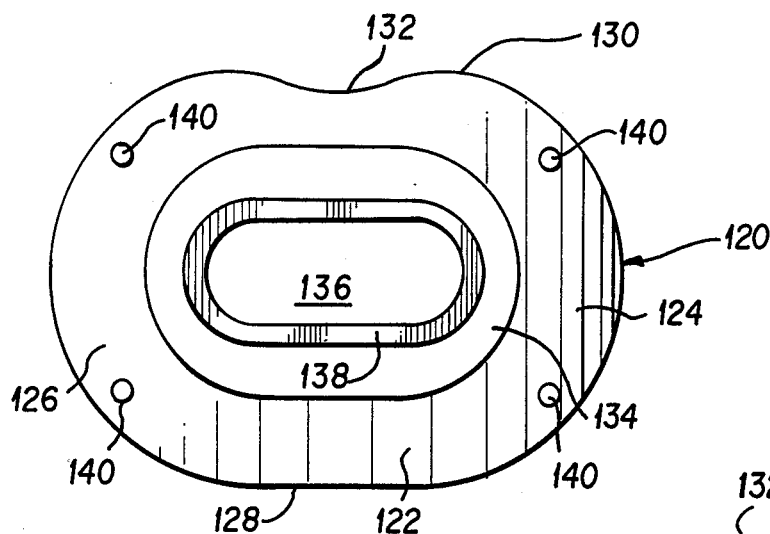
Figure 4:
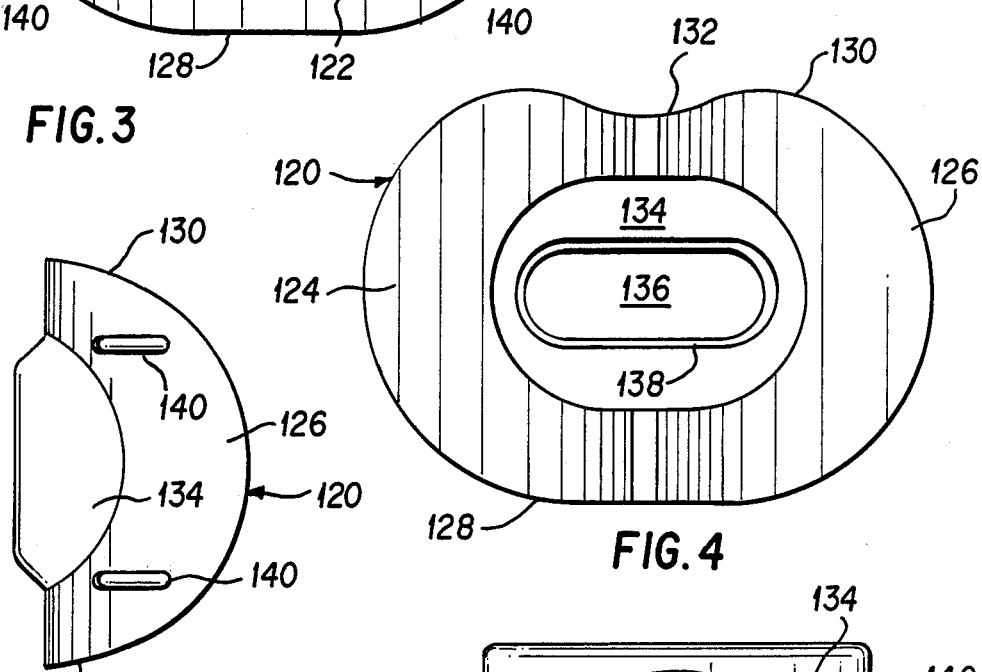
Figure 5:
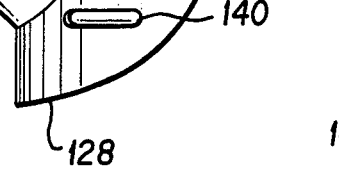

In FIGS. 3 and 4 it is seen that the oral mask is of a generally oval configuration having a lower edge 128 and an upper edge 130. In the upper edge 130 there is a recess or a nasal notch 132 so that the oral mask 120 can accommodate itself to the nose of an individual and and to avoid pressure thereaginst.

There is an outwardly projecting central housing 134. In the central housing 134 there is an opening 136. The opening 136 is of a generally oblong configuration. Surrounding the opening 136 is an O-ring 138.

On the outer surface of the sides 124 and 126 are four outwardly projecting pins 140. These pins 140 can be considered to be headstrap attachment pins. A head strap can be attached to these pins and positioned around the head of an individual so as to firmly hold the oral mask 120 in contact with the face of an individual, if necessary.

The inner surface of the sides 124 and 126 can be considered to be the facial contact area of the oral mask 120.

An oral airway 150 is illustrated in FIGS. 8–13 and FIG. 21.

The oral airway 150 comprises a dental contact segment 152 and a pharyngeal segment 154.

The dental contact segment 152 may also be considered to be an oral segment 152. The dental contact segment 152 has a front wall 156 and a rear wall 158. Also, there is a curved left side wall 160 connecting 156 and 158. Further, there is a curved right side wall 162 connecting 156 and 158.

There is a left central channel septum 164 having a left lower inter-communicating aperture 166 and a left upper inter-communicating aperture 168.

There is a right central channel septum 170 having a right lower inter-communicating aperture 172 and a right upper inter-communicating aperture 174.

The left central channel septum 164 and the curved left side wall 160 define a left lateral conduit 176.

The right central channel septum 170 and the curved right side wall 162 define a right lateral conduit 178.

The dental contact segment 152 has a upper wall 180. There is a ventilating side arm 182 at about a 45 degree angle with the upper top wall 180 and the curved left side wall 160. The ventilating side arm 182 is hollow and has a passageway 183 to allow the flow of fluid such as gas.

On the upper top wall 180 there is a neck or central channel housing 184.

Figure 12:
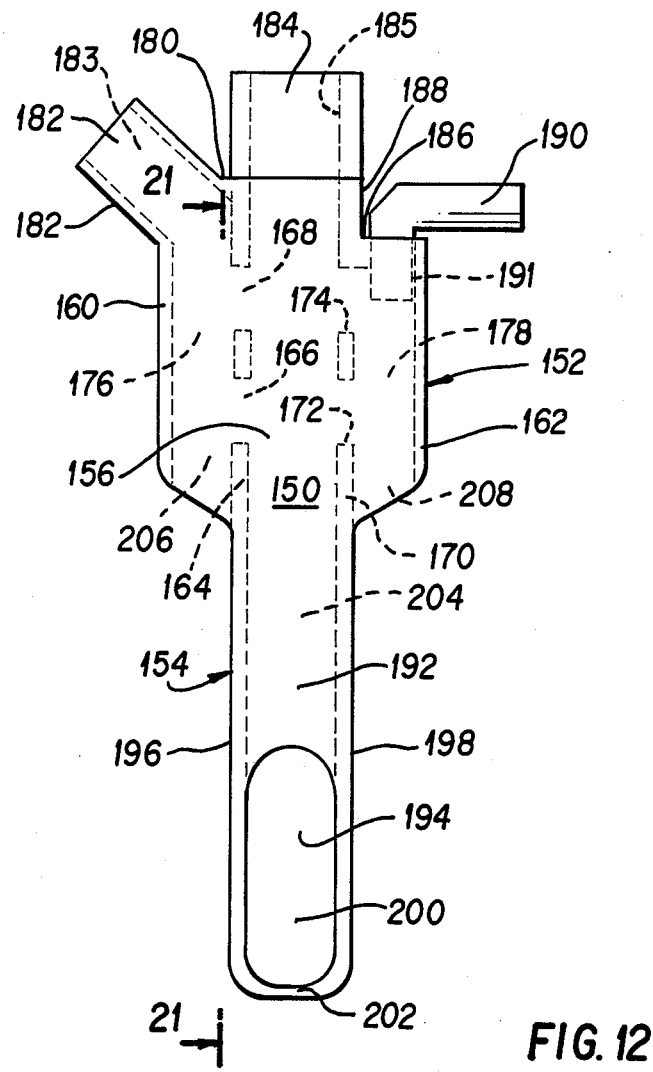
Figure 13:
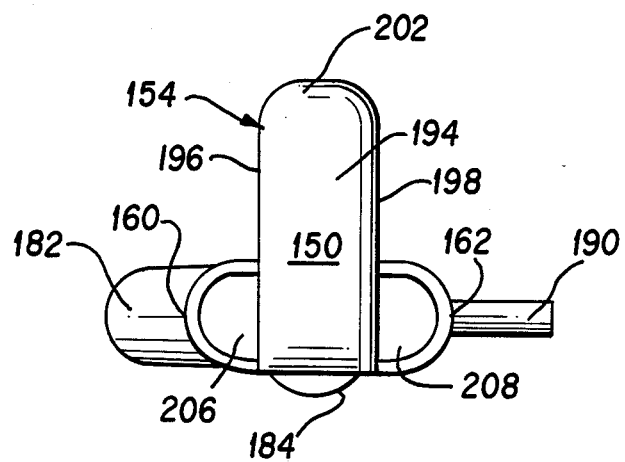
Figure 16:
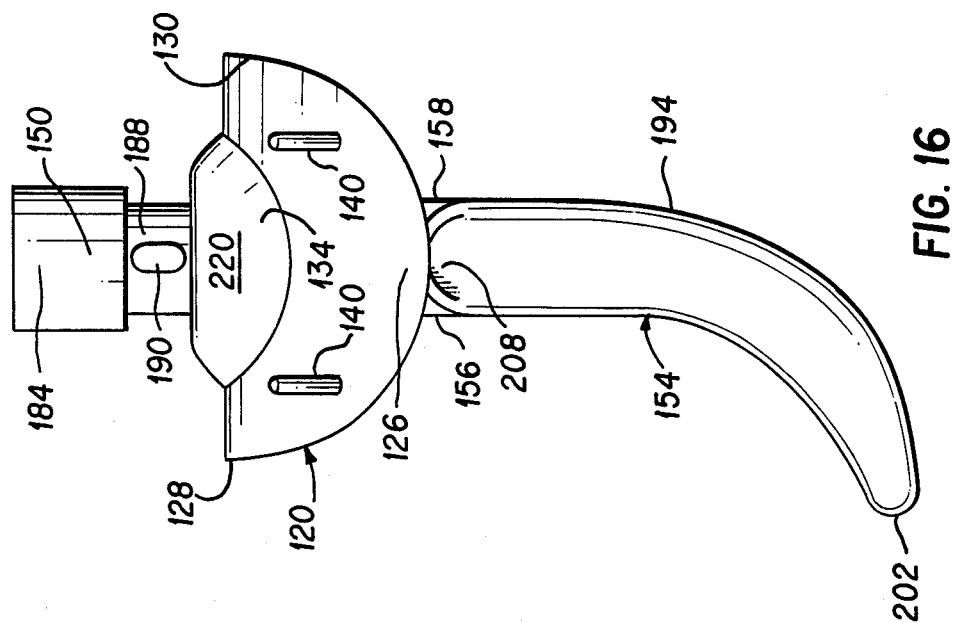
Figure 17:
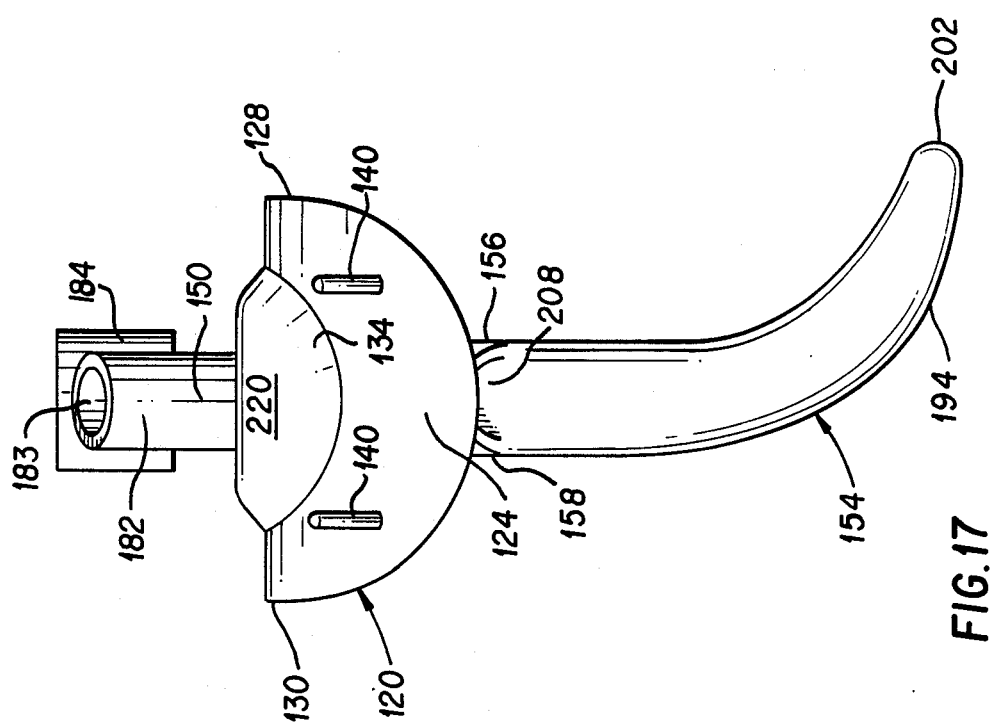
Figure 18:
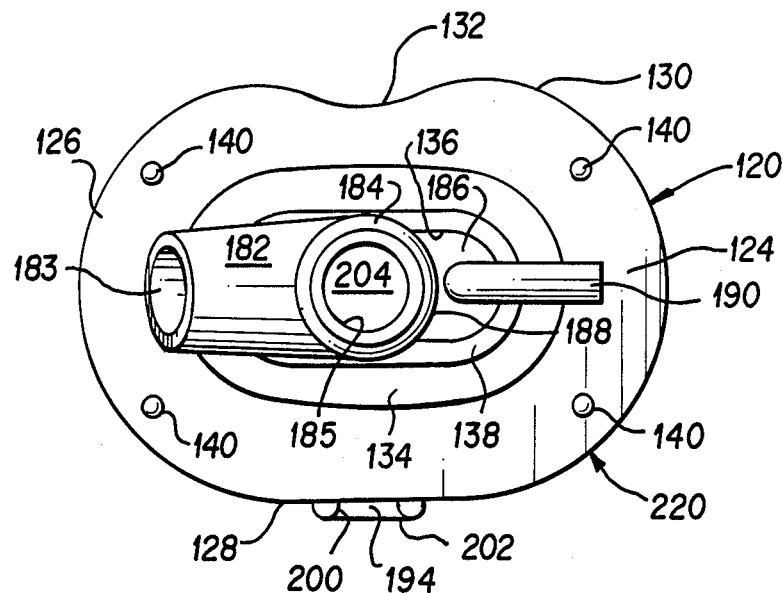
Figure 19:
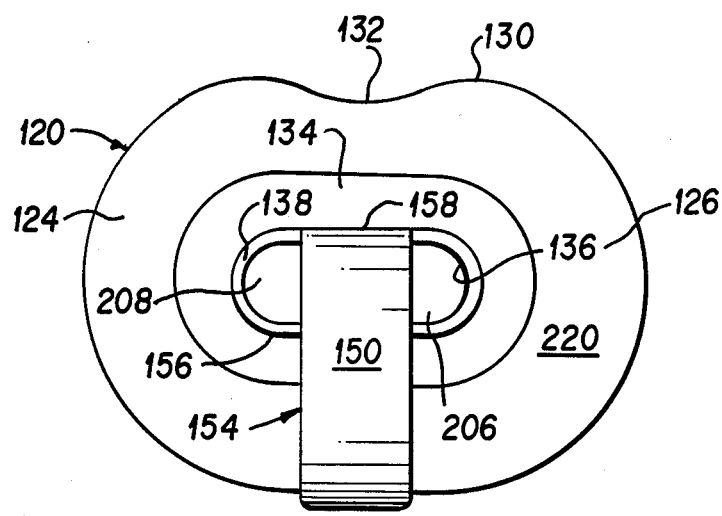

In FIG. 12 at the right and below the upper top wall 180 there is a deck 186. A wall 188 connects with the deck 186 and also with the upper top wall 180.

In the upper right part of FIG. 12 there is illustrated a suction channel plug 190. At the upper part of the right lateral conduit 178 there is an opening 191. The suction channel plug 190 is placed in the opening 191 and seals off the opening, when appropriate. The pharyngeal segment 154 has a front wall 192 and a rear wall 194. The flat left side wall 196 connects with the front wall 192 and the rear wall 194. A flat right side wall 198 connects with the front wall 192 and the rear wall 194.

In the lower part of the pharyngeal segment 154 and in the front wall 192 there is an outlet orifice 200. In FIG. 12 the outlet orifice 200 has a oblong appearance. On the lower end of the pharyngeal segment 152 there appears to be a lower tip or lower end 202.

The neck or central channel housing 184 is hollow and has a passageway 185 for connecting with the interior of the oral airway 150. The oral airway 150 has a airway central channel 204 which connects with the outlet orifice 200.

The ventilating side arm 182 is hollow and is at an angle of about 45 degrees with the upper top wall 180 and the curved left side wall 160. The ventilating side arm 182 functions as a conduit. The left lateral conduit 176 on its lower end has a left lateral conduit exit 206. Also, the left lateral conduit 176 by means of apertures 166 and 168 connect with the airway central channel 204.

The right lateral conduit 178 has a lower right lateral conduit exit 208. As previously stated, the suction channel plug 190 seals off the upper opening, when appropriate, of the right lateral conduit 178. The right lateral conduit 178 and the airway central channel 204 connect with each other by apertures 172 and 174.

In FIGS. 9 and 10 it is seen that the pharyngeal segment 154 curves and tapers and that the front wall 192 is a interior curved wall and that the rear wall 194 is an exterior curved rear wall. The front wall 192 is concave and the rear wall 194 is convex. The reason for the curved and tapered pharyngeal segment 154 is so that the oral airway 150 can fit more readily into the oropharynx behind the tongue of the patient.

It is to be noted that the ventilating side arm 182 tapers so that the outer end has a smaller cross-sectional dimension than the inner end.

The oral airway is designed to allow the passage of gases and vapors into and out of the oropharynx and hypopharynx of the patient.

The oral mask 120 and the oral airway 152 can be made of a plastic. A desirable plastic is a medical grade non-allergenic plastic. One such appropriate plastic is polyethylene. The surfaces of a polyethylene oral mask and a polyethylene airway are smooth and are compatible with the tissues of the patient.

In FIGS. 14–19 there is illustrated the combination 220 of the oral mask 120 and the oral airway 150.

The oral airway 150 has a pharyngeal area 154 which is of a smaller lateral dimension than the opening 136 defined by the O-ring 138.

The outer dimensions of the mid-section of the oral airway 150 are slightly greater than the inner dimensions of the O-ring 138. The mid-section of the oral airway 150 includes the dental contact segment 152.

The combination 220 can be assembled with the pharyngeal segment 154 pushed through the lubricated opening 136. This is easily accomplished. Then, the mid-section can be pushed into the O-ring 138 to the desired position. The O-ring 138 is flexible and makes an air tight seal around the mid-section of the oral airway 150. In FIGS. 14 and 15 it is seen that the nasal notch 132 of the oral mask 120 is on one side of the oral mask 120 while the pharyngeal segment 154 points downwardly in the other direction from the nasal notch 132. In other words, the nasal notch 132 is horizontal or close to the nose and the pharyngeal segment 154 is to be in the oropharynx of the patient.

The downward position of the oral airway 150 is impeded or the movement of the oral airway 150 is impeded, or limited by the lower surface of the ventilating side arm 182 with respect to the flat surface of the outwardly and upwardly protecting central housing 134.

There is the availability of some relative movement between the oral mask 120 and the oral airway 150. Since the positions of the oral mask 120 and the oral airway 150 can be varied with the position of the mid-section of the oral airway 150 in the O-ring 138 in the opening 136, it can be seen that the operating connection between the oral airway 150 and the oral mask 120 is not rigid. Since the O-ring is flexible, it is possible to change the position to a moderate degree of the oral airway tip 202 with respect to the oral mask 120 as well as to the larynx and hypopharynx. In addition, there is the possibility of considerable movement between the oral mask 120 and the oral airway 150 vertically because the oral airway can be moved upwards or downwards with respect to the oral mask and in one model I have prepared the range of movement of the oral airway with respect to the oral mask can be over 20 mm. The ability to have relative movement between the oral mask 120 and the oral airway 150 makes it possible for the combination 220 to be used with a variety of patients having varying physical configurations.

In FIGS. 22, 23, 62, 63 and 64 there is illustrated a species 230 of the oral mask. To the oral mask 120 there is added a pneumatic cushion 232. This pneumatic cushion 232 is in the same general configuration of an O-ring 234 having an opening 236. The O-ring 234 is operatively connecting with the inner surface of the oral mask 120. The O-ring 234 may be adhered to the inner surface of the oral mask 120 by means of an adhesive. The pneumatic cushion 232 is inflatable as there is a pneumatic valve 238. The opening 236 is around the periphery of the oral mask 120. The pneumatic cushion 232 effects a seal between the pneumatic cushion 232 and the peri-oral tissues. The pneumatic cushion 232 can be of varying intensities of pressures due to the amount of gas used to inflate the cushion. The pneumatic cushion should, preferably, be of soft consistency for comfort to the patient and to effect a better seal with the peri-oral tissue. In FIG. 22 it is seen that the pneumatic cushion 232 is of a V-configuration because of the conformance of the cushion 232 to the configuration of the oral mask 120. Also, in FIG. 23 the pneumatic cushion 232 conforms to the configuration of the oral mask 120.

In FIG. 1 there is illustrated a combination 220 of the oral mask 120 and the oral airway 150. It is seen that the pharyngeal segment 154 is in the oropharynx of the head 100 of the patient. Also, it is seen that two of the four pins 140 are illustrated. It is to be understood that a head-strap can be connected to these four pins to hold the oral mask 120 firmly against the peri-oral tissues of the individual patient. The reader is to recall that in FIG. 3 that there are four pins 140. With the view of FIG. 1 only two of the pins are illustrated.

Figure 24:
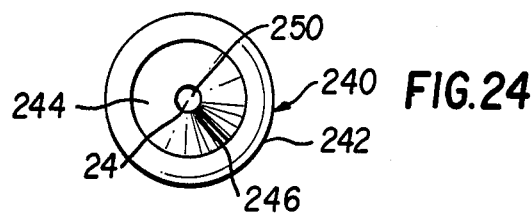
Figure 25:
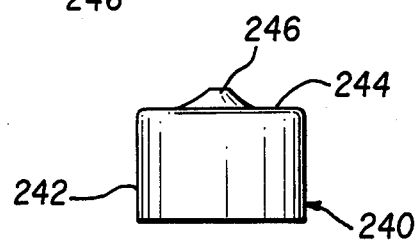

In FIGS. 24 and 25 there is illustrated a Universal ET Tube Connector 240. The tube connector 240 comprises a cylinderical side wall 242 and an end wall 244. The central part of the end wall 244 is thinner than the periphery of the end wall. Also, in the central part of the end wall there is a distensible central nipple 246. In 246 there is a passageway 248. The tube connector 240 has a hollow interior 250.

The material of the construction of the tube connector 240 is a flexible elastomer. The end wall 244 can be pushed inwardly to occupy part of the hollow interior 250.

Figure 27:
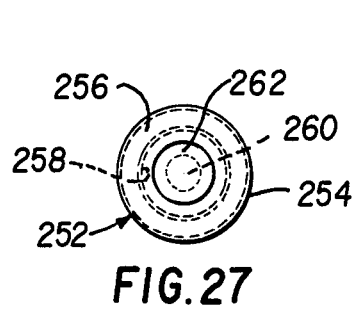
Figure 28:
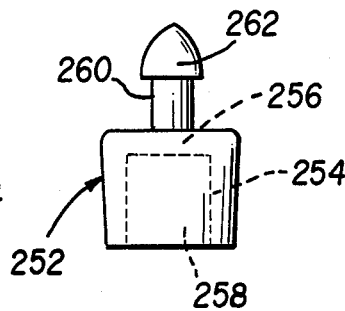
Figure 26:
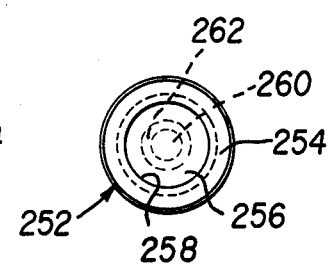

In FIGS. 26, 27 and 28 there is illustrated a plug and cap unit 252. This unit comprises a side wall 254 and an end wall 256. The unit has a hollow interior 258. Projecting outwardly of the end wall 256 is a stem 260. On the end of the stem 260 there is an enlarged cap 262 or a button 262. The exterior diameter of the enlarged cap 262 is larger than the diameter of the stem 260 so as to give the appearance of a toad-stool or the stem 260 in conjunction with the cap 262 appears as a toad-stool in FIG. 28. The side wall 254 tapers inwardly from the exterior toward the end wall 256. The hollow interior has a 15mm interior dimension taper female slip joint and the side wall 254 has a 22mm outside diameter taper male slip joint. In FIGS. 26–28 there is illustrated the taper of the side wall from the exterior as it goes toward the end wall 256. The material construction of the plug and cap unit 252 can be polyethylene or ethylene vinyl acetate. The material of construction of the plug and cap unit 252 should be non-allergenic medical grade plastic.

Figure 29:
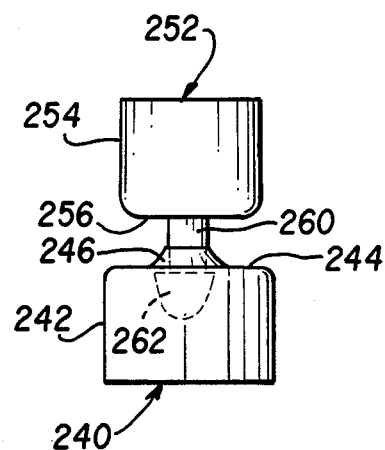
Figure 33:
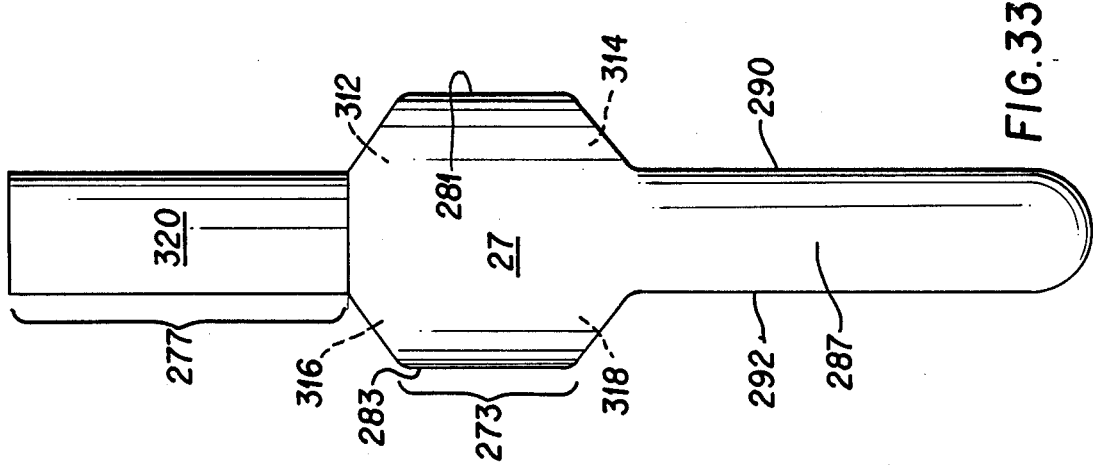

In FIG. 29 there is illustrated the combination of the tube connector 240 and the plug and cap unit 252 with the stem 260 in passageway 248. The plug and cap unit 252 is used to seal off the passageway 248, when needed. In FIG. 29 the end wall 244 of the connector 240 is spaced apart from the end wall 256 of the plug and cap unit 252.

Figure 30:
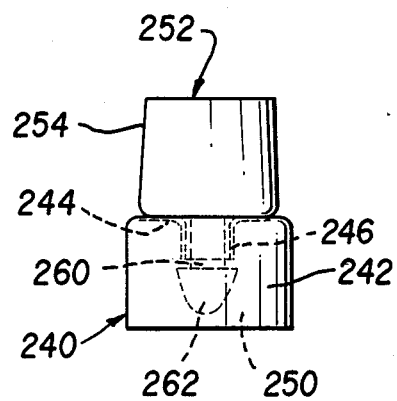
FIGS. 29 and 30 are of a combination of the Universal ET tube connector and the plug and cap unit wherein the stem of the plug and cap unit is in the passageway of the ET tube connector and the ET tube connector and the plug and cap unit are spaced apart.

In FIG. 30 there is illustrated a combination of the tube connector 240 and the cap unit 252 with the end wall 244 juxtapositioned to the end wall 256. In fact, the end wall 256 and the cap unit 252 is pressing against the end wall 244 of the tube connector 240 so as to press inwardly the end wall 244 into the hollow interior 250 with the tube connector 240. Again, the stem 260 is in the passageway 248 of the tube connector 240.

With reference again to FIG. 1 it is seen that the oral airway 150 is positioned in the oral cavity 108 of the patient.

On the upper part of the oral airway 150 it is seen that there is a ventilating side arm 182. There is positioned on the ventilating side arm 182 a breathing circuit elbow which is shown in the inset drawing. The reader is to understand that the breathing circuit elbow is illustrated in FIG. 2 by reference numeral 356 and will be described in a later part of the specification.

There is positioned over the neck of the central channel housing 184 of the oral airway 150 a Universal ET tube connector 240, identified as an airway port. In the passageway 248 of the connector 240 there is positioned an endotracheal tube 269. On the upper end of the tube 269 there is positioned another Universal ET tube connector 240 identified as a middle connector. Again, the endotracheal tube 269 is in the passageway 248. In the hollow interior 250 of the connector 240 there is positioned a fiberoptic bronchoscope adapter 270. This adapter 270 has a body 272. There is a side arm 274 on the body 272. The side arm 274 is essentially a tube and has a passageway. A plug and cap unit 252 can fit over the end of the side arm 274 to seal the side arm 274. A pressure relief port 273 is covered with adhesive tape during use to prevent gas leakage.

On the upper end of the fiberoptic bronchoscope adapter 270 there is another Universal ET Tube Connector 240 identified as the upper port. There is positioned in the passageway 248 of the connector 240 a flexible fiberoptic scope 276. The reader upon reviewing FIG. 1 sees that the flexible fiberoptic scope 276 passes through the fiberoptic bronchoscope adapter 270, the endotracheal tube 269, the oral airway 150 and into the trachea 112 of the patient and projects beyond the end of the oral airway 150 into the trachea 112.

Also, there is positioned in the passageway 248 of the Universal ET Tube Connector 240 in the neck or central channel housing 184 of the oral airway 150 an ET tube cuff-inflating tubing 282. The cuff-inflating tubing 282 connects with an indicator bag 284 which in turn is part of an air seal unit 286. The air seal 286 accepts a syringe 280.

In the trachea 112 and surrounding the endotracheal tube 269 there is a tracheal tube cuff 288 which is shown in an inflated condition merely for purposes of illustration.

Figure 20:
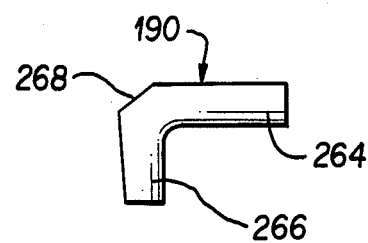
FIG. 20 is a view of the suction channel plug.
Figure 21:
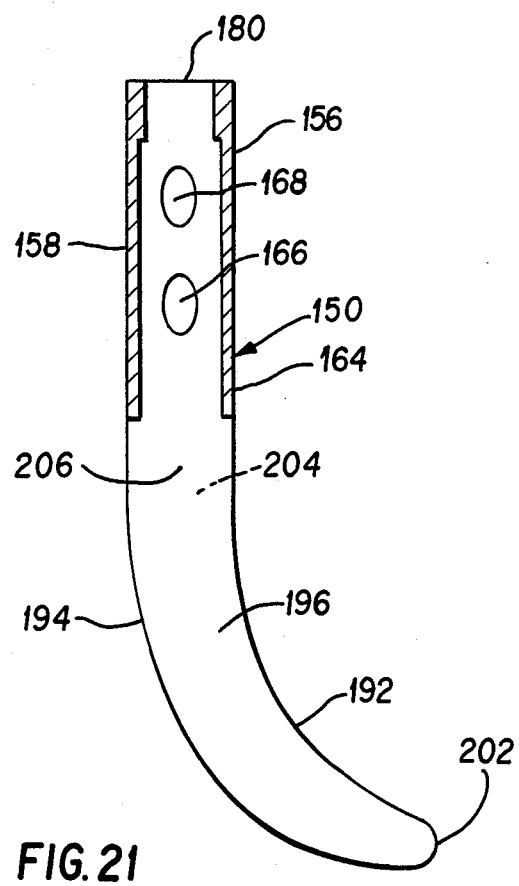
FIG. 21 is a fragmentary cross-sectional view taken on line 21—21 of FIG. 12 of the septum of the oral airway showing the enter communicating apertures which are housed within the dental contact zone.

In FIG. 20 there is illustrated the suction channel plug 190. The plug 190 comprises a handle part 264 and a plug part 266. The handle part 264 and the plug part 266 are, substantially, at a right angle to each other. On the outer part of the plug 190 there is a flat surface 268 between the handle part 264 and the plug part 266. The plug part 266 tapers so that the outer or free end is of a smaller dimension than the inner end close to the handle part 264. The taper assures a tight seal between the plug 190 and the suction channel opening 191. The plug can be made of medical grade non-allergenic polyethylene.

With reference to FIG. 1 the endotracheal tube 269 with its tracheal tube cuff 288, cuff-inflating tube 282, indicator bag 284, as well as the syringe 280 are commercially available. All of these, except the syringe 280 are an assembled unit and are integral. The syringe 280 is a standard syringe and is commercially available. In FIG. 1 it is seen that the cuff inflating tubing 282 is positioned in the wall of the endotracheal tube 269. With the actuation of the syringe 280 the tracheal tube cuff 288 can be expanded so as to seal the trachea against a gas leak or a fluid leak around the tube 269. With the tube cuff 288 properly positioned and expanded so as to press against the wall of the trachea 112 it is usually not possible for gas or fluid to leak around the tube cuff 288 and to rise into the oropharynx 289, or for fluid to go from the oropharynx into the trachea. The expanded tube cuff 288 insures that the gas, both intake and exhaust gas, flows within the lumen of the endotracheal tube 269. The reader is to understand that with the fiberoptic scope in the lumen of the endotracheal tube 269 the tracheal tube cuff 288 is not expanded. This allows gas, both inflow and outflow gas, to flow around the tube cuff 288 and into and out of the trachea. After the endotracheal tube 269 and the tracheal cuff 288 are properly positioned in the trachea the fiberoptic scope 276 can be withdrawn from the endotracheal tube 269. Then the tracheal tube cuff 288 can be expanded to contact the wall of the trachea, following which the flow of gas, both inflow and outflow gas, is within the endotracheal tube 269. By way of recapitulation the oral airway 150 is placed in the oral cavity of the patient. The endotracheal tube 269 is placed in the oral airway 150 and finally into the trachea 112. The fiberoptic scope 276 is used to position the endotracheal tube 269 at the desired location in the trachea 112. At this time the tracheal tube cuff 288 is not expanded so as to contact the wall of the trachea 112. This allows gas such as inflow and outflow gas to flow around the tracheal tube cuff 288. Inflow and outflow gas flow through the ventilating side arm 182 into the oral cavity 108 and also within the left lateral conduit 176 and the airway central channel 204 of the oral airway. With the endotracheal tube 269 in the airway central channel 204 the gases flow mainly through the left lateral conduit 176 and the ventilating side arm 182. After the endotracheal tube 269 has been positioned in the trachea 112 with the aid of the fiberoptic scope 276, the fiberoptic scope 276 is withdrawn from the endotracheal tube 269. The tracheal tube cuff 288 is expanded to contact the trachea 112 to prevent the flow of gas to and from the oral cavity 108 of the patient and around the tracheal tube cuff 288. Then, the flow of gas, both the inflow and outflow gases, now flows through the endotracheal tube 269 to and from the trachea 112. With the ET tube positioned within the airway central channel the left lateral conduit 176 is used for the flow of gas to and from the trachea before the tracheal tube cuff 288 is expanded to contact the trachea 112. After the tracheal tube cuff 288 has been expanded, and the endotracheal tube 269 connected to the gas supply, the flow of gas is through the endotracheal tube 269. The ventilating side arm, as well as the left lateral conduit 176, no longer function. With the endotracheal tube 269 positioned within the airway central channel 204 the channel is blocked to a degree for the flow of gas but there is some gas flowing from the left lateral conduit 176 by means of the intercommunicating apertures 166, 168, 172 and 174 to the right lateral conduit 178 and also through the airway central channel 204 and into the trachea 112 before the tracheal tube cuff 288 is expanded. Larger ET tubes allow less cross-over ventilation between the left lateral conduit 176 and the airway central channel 204 while the smaller tubes allow more cross-over ventilation depending upon the size of the airway and its central channel.

In FIGS. 31, 32, 33, 34, 35 and 36 there is illustrated another species of an oral airway identified with reference numeral 271.

The oral airway 271 has a dental contact zone 273, a pharyngeal zone 275 and a neck zone 277.

In the dental contact zone 273 there is a front wall 278 and a rear wall 279. A curved left side-wall 281 connects with the front wall 278 and the rear wall 279. A curved right side-wall 283 connects with a front wall 278 and a rear wall 279.

Figure 32:
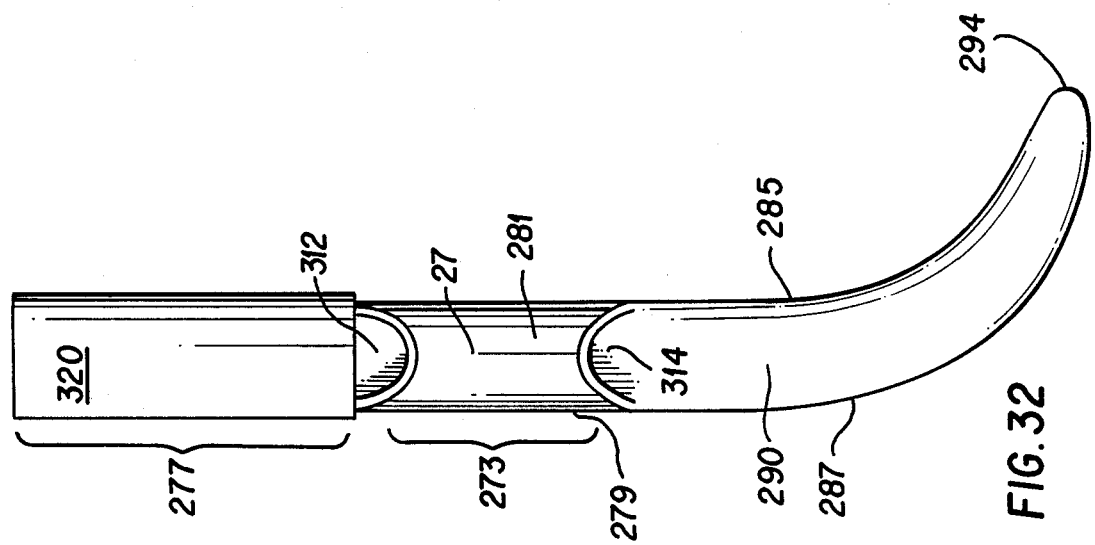
Figure 31:
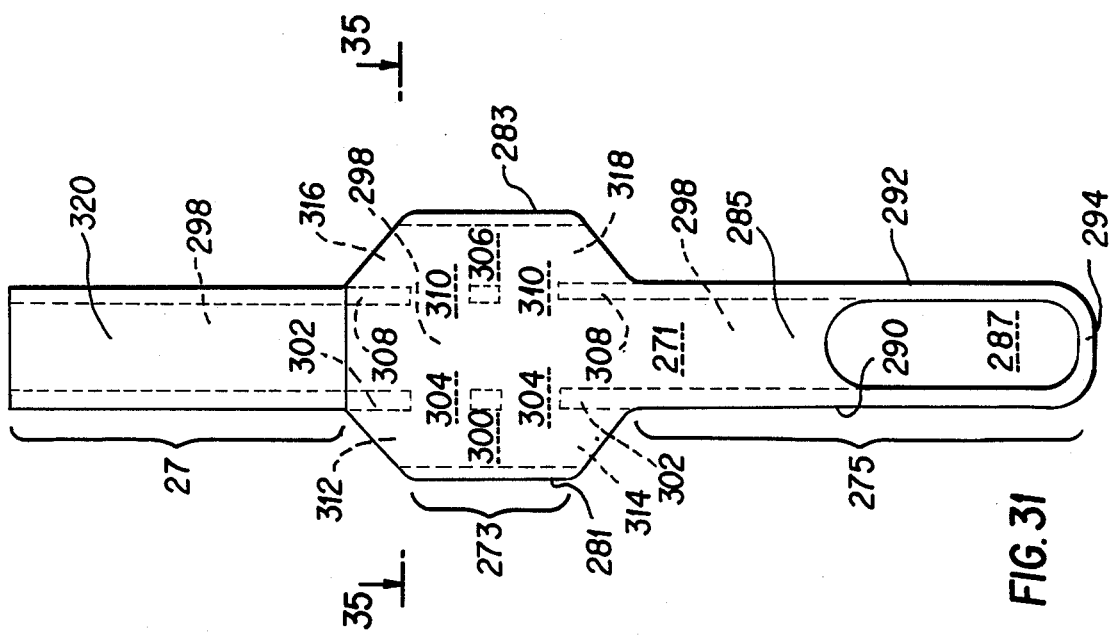
Figure 36:
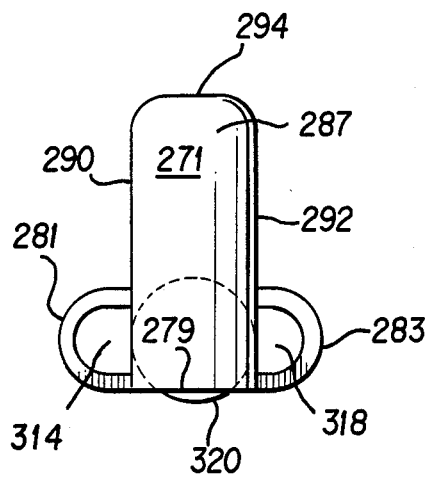
FIG. 36 is a bottom plan view.
Figure 35:
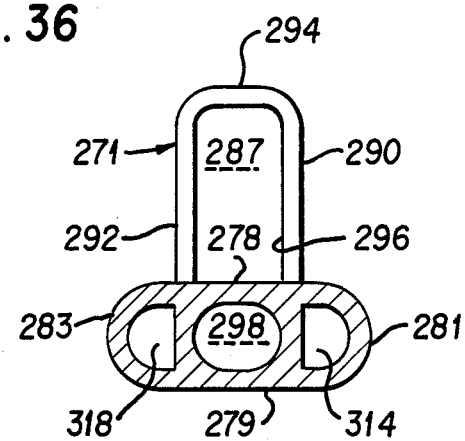
FIG. 35 is a lateral cross-sectional view in the dental contact zone of the oral airway.
Figure 34:
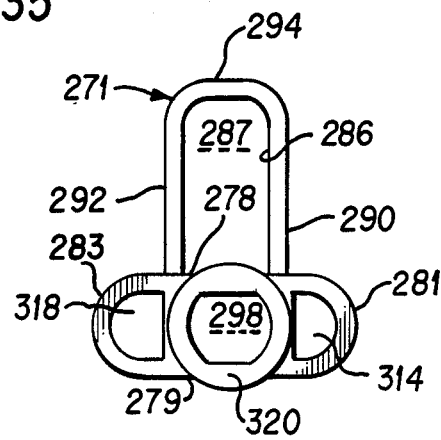
FIG. 34 is a top plan view of the oral airway.

In the pharyngeal zone 274 there is a front wall 285 and a rear wall 287. A left side-wall 290 connects with the front wall 285 and the rear wall 287. A right side-wall 292 connects with the front wall 285 and the rear wall 287. The pharyngeal zone 275, as viewed in FIG. 32, shows a curve. At the lower end of the curve and in the front wall 285 there is a lower tip or lower end 294. In the front wall 285 and near the free end or the lower end there is an outlet orifice 296 which is in an oblong configuration.

In the dental contact zone 273 and in the pharyngeal zone 275 and also in the neck zone 277 there is an airway central channel 298.

In the dental contact zone 273 there is a left lateral conduit 300 defined by the curved left side-wall 281 and a left central channel septum 302. In the septum 302 there are left intercommunicating apertures 304 intercommunicating between the left lateral conduit 300 and the airway central channel 298.

In the dental contact zone 273 there is a right lateral conduit 306 defined by the curved right side-wall 282 and a right central channel septum 308. In the septum 308 there are right intercommunicating apertures 310 intercommunicating the right lateral conduit 306 and the airway central channel 298.

In the upper part of the dental contact zone 273 there is an upper left opening 312 and in the lower part there is a lower left opening 314

Also, in the dental contact zone 273 there is a right upper opening 316 and a right lower opening 318.

A neck 320 connects, with the dental contact zone 273.

The oral airway 271 can be made of a suitable medical-grade, nonallergenic plastic such as polyethylene.

I have made one of these units and some of the dimensions are: the length of the neck is 55 mm's with 20.5 mm outside diameter. The inside lateral diameter of the airway central channel 298 in the neck is 15 mm's. The pharyngeal zone 274 has a 22 mm outside lateral diameter and the width of the opening in the outlet orfice 296 is 15 mm's inside diameter. The length of the pharyngeal zone 274 is about 78 mm's. The thickness of the dental contact zone is about 17 mm'.

Figure 37:
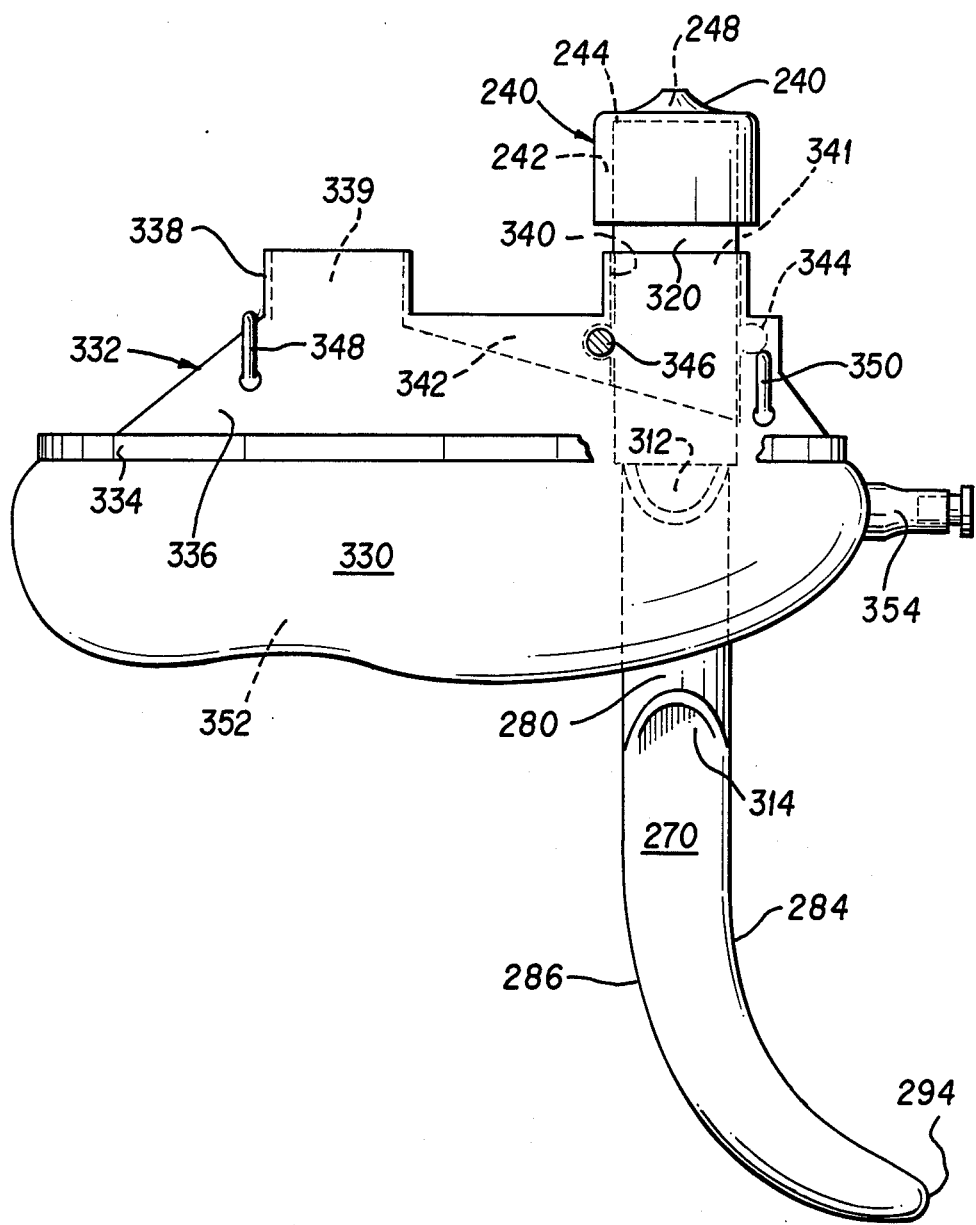
Figure 38:
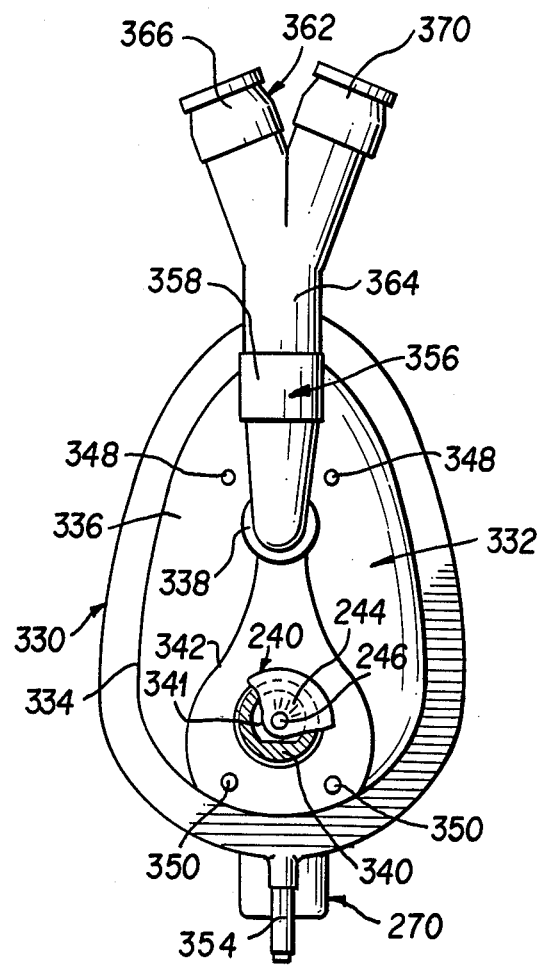
Figure 39:
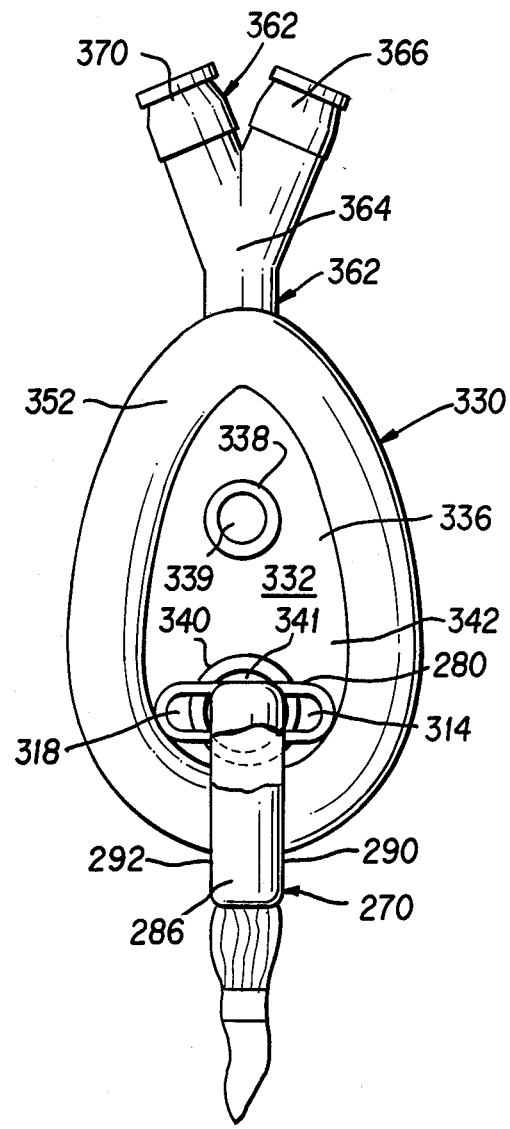

In FIGS. 37, 38 and 39 there is illustrated a modified plastic face mask 330.

The face mask 330 comprises a mask body 332 of a transparent hard plastic. On the lower part of the mask body 332 there is an encircling outwardly directed cushion mount 334. The mask body 332 comprises curved sloping sides 336. The sides 336 slope upwardly and inwardly to form a rear mask chimney 338 having a passageway 339. Also, the sides 336 slope upwardly and inwardly and form a front airway chimney 340.

From the forward part of the rear mask chimney and extending past the forward part of the front airway chimney 340 and down to the encircling cushion mount 334 there is a reinforced region 342. The front airway chimney 340 is in this reinforced region 342. The chimney 340 defines an airway receiving channel 341. In the channel 341 and in the interior of the face mask 330 there is a recess 344 for seating O-ring 346.

In FIG. 38 and partially in FIG. 37 it is seen that there are two rear head-strap attachment pins 348 and also two front head strap attachment pins 350.

There is attached to the underneath surface of the cushion mount 334 a flexible inflatable cushion 352. In FIG. 39 it is seen that the cushion is of a somewhat oblong configuration. In FIG. 37 it is seen that there is an air inlet 354 for the cushion 352. The air inlet 354 makes it possible to inject air into the cushion 352 to inflate the cushion to its correct volume and shape.

In FIGS. 38, 39 and 2 there is illustrated a breathing circuit elbow (mask elbow) 356 having a receiving end 358 and a projecting end 360. There is attached to the elbow 356 a breathing circuit Y-piece 362 having a projecting body part 364, a first breathing hose limb 366 for receiving corrugated breathing hose 368 and a second breathing hose limb 370 for receiving corrugated breathing hose 372.

The projecting end 360 inserts tightly into the rear mask chimney 338. Again, in the chimney 338 there is a passageway 339 for the flow of a gas. The projecting body part 364 of the Y-piece fits into and is received by the receiving end 358 of the breathing circuit elbow 356.

There is a commercially available face mask having a mask body, a rear mask chimney, a cushion mount and a flexible cushion. My improvement is the addition of the front airway channel, a reinforced region adjacent to the front airway chimney, a recess for seating an O-ring and said O-ring.

In FIG. 2 there is illustrated the modified plastic face mask 330 on the head 100 of the patient. The mask 330 is positioned over the nose 104 and mouth of the patient. The flexible inflatable cushion 352 conforms to the anatomical configuration of the patient's face. There are elastic straps 374, in phantom, connecting with the head-strap attachment pins 348 and 350 so as to securely position the face mask 330 onto the patient's face.

The reader is to understand that the face mask 330 may be used without the oral airway 271 in position in the mask 330. In FIG. 2 there is illustrated the oral airway 271 in the airway receiving channel 341 and the breathing circuit elbow (mask elbow) 356 in the mask chimney 338. Without the oral airway 271 positioned in the airway receiving chimney 341 the channel 341 is sealed by means of the plug and cap unit 252.

With the airway receiving channel 341 plugged, the mask chimney 338 has positioned in it the breathing circuit elbow 356 which connects to an anesthesia machine 376 by means of Y-piece 362 and two corrugated breathing hoses 368 and 372. This is the source of the inhalation anesthetic for the anesthetization of the patient or for the administration of oxygen prior to the anesthetization of the patient.

As soon as the patient is sufficiently anesthetized to accept the placement of the oral airway 271 into the oral cavity 108 and the oropharynx 289 the face mask 330 is removed from the patient. Then, the oral airway 271 is inserted into the airway receiving channel 341 of the face mask 330. The neck 320 of the oral airway 271 is inserted into the airway receiving channel 341. Then, the Universal ET Tube Connector 240, (an airway port) with its distensible port is plugged with a plug and cap unit 252 placed on top of the neck 320. Naturally, in the time period when the oral airway 271 is being placed in the airway receiving channel 341 the face mask 330 is removed from the head 100 of the patient. In this time period, if the patient is breathing spontaneously, the effects of the anesthesia may lighten somewhat. The oral airway 271 is positioned in the oral cavity 108 and the oropharynx 289 as expeditiously as possible and the face mask 330 is seated on the face of the patient. Then, additional anesthesia can be administered and the anesthetic deepened to the desired depth. With the patient under the proper depth of anesthesia the plug and cap unit 252 can be removed from the tube connector 240, the airway port. At this time it is possible to insert the endotracheal tube 269 into the oral airway 271 or to insert the combination of the endotracheal tube 269 and the flexible fiberoptic scope 277, simultaneously, into the oral airway 271 and into the trachea 112 of the patient. A third alternative is to have the endotracheal tube positioned over the upper part of the flexible fiberoptic scope 271 but not in the oral airway 271. The fiberoptic scope 277 can be passed into the oral cavity 108 and into the trachea 112 of the patient for examination purposes. After the examination purpose the endotracheal tube 269 can be passed over the fiberoptic scope 277 and into the oral airway 271.

There are five ways the airway 271 can interact with an endotracheal tube 269 and a flexible fiberoptic scope 276:

FIRST, A flexible fiberoptic scope 276 can be passed through the airway, then into the hypopharynx and finally into the trachea and lower respiratory tract, if desired, for purposes of examination and/or treatment.

SECONDLY, An endotracheal tube 269 may be passed blindly, directly through the airway 271 and into the trachea 112, without the use of the fiberscope.

THIRDLY, An endotracheal tube 269 may be positioned over the upper end of the fiberoptic scope 276 after which the fiberoptic scope 276 is passed through the airway 271 and thence into the trachea following which the ET tube 269 is passed over the scope 276 and into the trachea. The scope 276 may then be used to check for correct placement of the ET tube, and then is removed.

FOURTHLY, An ET tube 269 may be passed into the airway 271, following which the fiberoptic scope 276 is passed through the ET tube 269 and into the trachea. The tube is then advanced over the scope into the trachea and the scope is removed.

FIFTHLY, The airway may be 'PRE-LOADED' as follows:

The ET tube connector is removed from the tube. If necessary, it may be cut off of the tube. The BRONCHOSCOP-AID is slipped over the proximal end of the ET tube. Alternatively, if the ET tube connector is not to be removed at this time, then a UNIVERSAL ET TUBE CONNECTOR is removed from the lower end of the BRONCHOSCOP-AID, and that end of the adaptor is attached to the ET tube connector. The side arm of the adaptor is capped with A PLUG AND CAP UNIT and its pressure relief port covered with tape to prevent loss of gas and vapors.

The FFS is now inserted into the UPPER PORT, passed through the BRONCHOSCOP-AID and down the ET tube until the tip of the FFS rests just past the beveled end of the ET tube. Its free passage is checked out by moving it up and down the tube several times before the final positioning.

The thoroughly lubricated endotracheal tube is passed through the AIRWAY PORT, and into the central channel of the airway, its distal end being allowed to protrude just past the tip of the airway. If the patient has 'snaggy' teeth, the tube's cuff is kept hidden (and protected) in the central channel until after the airway has been safely placed in the oral cavity. Its free passage, likewise, is checked out by moving it up and down the central channel before final positioning.

In FIGS. 40–47 there is illustrated an airway 380. The airway 380 is a take-apart airway. The airway comprises a body portion 382 and a spline 384.

The body portion 382 has a pharyngeal segment 386, a dental contact zone 388 and a cross-over communication channel housing 390. On the upper part of the body 382 there is a neck 392 having a passageway 394.

In FIG. 42 and on the upper right part of the body 382 there is a ventilating side arm 396 having a passageway 398.

Figure 41:
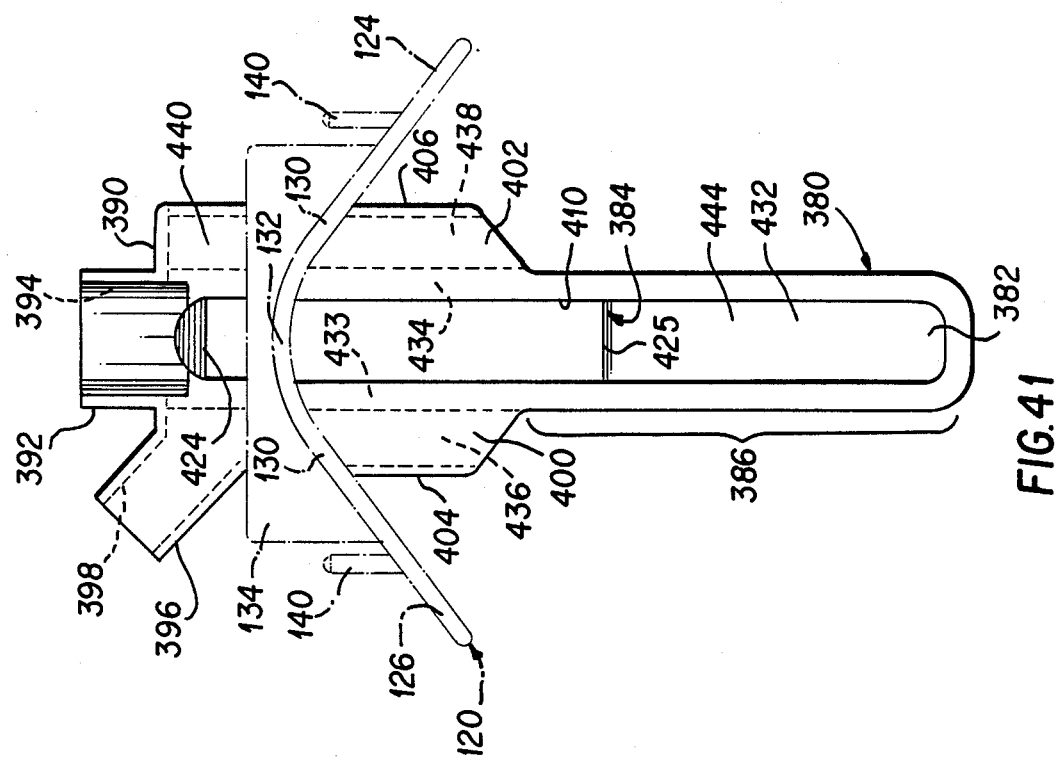

With reference to FIG. 41 it is seen that there is a left front wall 400, a right front wall 402, a curved left side wall 404 and a curved right side wall 406. Also, the oral airway 380 has a back wall 408.

In FIG. 41 it is seen that there is a spline channel 410. In FIG. 40 it is seen that there is a left wall 412 having a left keyway 414 for contact with the spline 384. Also, it is seen that there is a right wall 416 having a right keyway 418 for contact with the spline 384.

In FIGS. 44 and 47 it is seen that the spline 384 has a main body 420 and in FIG. 47 at the right end there is a spline neck 422. The spline neck 422 is thicker than the main body 420. Also, on the inner end of the spline neck 422 there is a finger grip bevel 424. At the free end of the main body 420 there is a bevel 425.

On each side of the main body 420 there is a key 426. On the spline neck 422 and near the upper surface there is a lip 428 on each side. The lip 428 is illustrated in FIGS. 44 and 47. Between the lip 428 and the key 426 there is a recess 430. In FIGS. 44 and 47 there is illustrated the lip 428. Also, the left wall 412 and the right wall 416 of the body 382 are received in the recesses 430 of the spline 384. The body 382 in the upper part has skid areas 29 on each side of the spline channel 410. The lips 428 can slide on and move over the skid areas 429. In FIGS. 44 and 45 it is seen that in the interior portion of the spline 384 there is a concave curve 431. The concave curve 431 in conjunction with the posterior wall 432 of the airway central channel 394 in the body 382 forms a passageway for the flexible fiberoptic scope 276. This is illustrated in FIG. 44. In FIG. 43 there is illustrated the body 382 without the spline 384. The airway central channel 394 accepts the endotracheal tube 269 after the spline 384 has been removed from the body 382 see FIG. 43.

In FIG. 41 there is illustrated, in phantom line, a left central channel wall 433 and a right central channel wall 434. The left central channel wall 433 in conjunction with the left front wall 400 defines the left lateral conduit 436. The right central channel wall 434 in conjunction with the curved right wall 406 defines a right lateral conduit 438.

In FIGS. 40, 41, 42, 43 and 44 there is illustrated a cross-over communicating channel 440. The cross-over communicating channel 440 communicates with the passageway 398, the right lateral conduit 438 and the left lateral conduit 436. In the region of the passageway 398, the left lateral conduit 436 and the communicating channel 440 there is a confluence region 442.

In FIGS. 41, 43 and 44 it is seen that there is a central channel outlet 444. The posterior wall 432 is also the rear visible wall in the central channel outlet 444.

In FIGS. 43-46 there is illustrated the airway central channel 446.

In FIG. 1 there has been illusteated and discussed the use of oral airway 150 and the oral mask 120. Therefore, the comments with respect to the oral airway 150 in FIG. 1 are also applicable to the oral airway 380. The oral airway 380 and oral mask 120 can be substituted in FIG. 1 for the oral airway 150 and oral mask 120 and placed in the head 100 of the patient as described in the foregoing part of this specification.

Reference numeral 446 is assigned to the airway central channel defined by the concave curve 431 of the spline 384 and the posterior wall 432 of the body 382.

In FIG. 41 there is illustrated the combination of the oral airway 380 and the oral mask 120.

In regard to assemblying the airway 380 reference is made to the following procedure:
 1. The spline 384 is lubricated with sterile, water-soluble lubricant.
 2. The spline 384 is inserted into the spline channel 410, to its full depth.
 3. A UNIVERSAL ET TUBE CONNECTOR (Dryden), hereinafter called the AIRWAY PORT 240 is attached firmly over the upper end of the oral airway 380 central channel housing 446 of the airway central channel 394 thereby maintaining the spline 384 in fixed position.
 4. The dental contact zone 388 and the pharyngeal segment of the airway 380 are lubricated with mineral oil or sterile water-soluble lubricant.
 5. The oral mask 120 is positioned so that the NASAL NOTCH faces the nose 104 of the patient.
 6. The oral airway 380 is inserted through the mask O-ring 138 aperture until the mask 120 is in the highest position on the body of the airway.

In regard to the removal of the airway 380 after satisfactory entry into the trachea 112 of the endotracheal tube 269, reference is made to the following procedure:
 1. The airway port 240 is removed from the neck 392 of the airway 380, then slid upwards to the upper end of the ET tube 269.
 2. The spline 384 is grasped by the finger grip bevel 424 and carefully pulled out of the spline channel 410.
 3. The pre-cut (shortened) ET tube 269 is advanced over the flexible fiberoptic scope (FFS) 276 well into the airway central channel.
 4. The FFS 276 is advanced further into the trachea 112 until the tracheal rings (not shown) or the carina (not shown) are positively identified.
 5. The ET tube 269 is advanced over the flexible fiberoptic scope 276 well into the trachea 112. Care is taken to avoid snagging of the ET tube cuff 288 by the lower teeth.
 6. Oxygen and anesthetic gases continue to be supplied to the patient's lungs by way of the airway 380 around the ET tube 269 and into the patient's trachea 112.
 7. The FFS 276 is removed from the ET tube 269.
 8. The breathing circuit elbow 356 is disconnected from the airway ventilating side arm 182, then attached to the bronchoscope adaptor side arm 274, the pressure relief port of the adaptor being covered with tape. Ventilation now continues directly through the ET tube 269 either before or after inflation of the ET tube cuff 286.
 9. After satisfactory oxygenation is assured, the airway port and the fiberoptic bronchoscope adaptor 270, along with the upper and middle connectors 240, are detached from the ET tube 269.
 10. The ET tube connector 240 is re-inserted into the proximal end of the ET tube 269.
 11. The breathing circuit elbow is disconnected from the bronchoscope adaptor side arm 274, then connected immediately to the ET tube connector and ventilation continued.
 12. The head-strap 374, is disconnected from the head-strap attachment pins 140 of the face mask 120.
 13. With the ET tube 269 securely held in a forward position (toward the chin) by an assistant, if necessary, the mask 120 and the airway 380 are carefully removed from the mouth 108, first with an upward and then a forward movement of the airway 380.
 14. If there is inadequate space in the airway central channel 394 for the initial passage of the ET tube 269, then the airway 380 must first be removed over the flexible fiberscope 276, following which the ET tube 269 is advanced over the scope 276 into the trachea. Ventilation will be briefly interrupted during this period.
 15. The patient should be well relaxed during these procedures.

A second procedure for removal of the airway 380 after satisfactory entry into the trachea 112 by the endotracheal tube 269 is as follows:

Procedures 1 through 12 are the same as those used in the preceding first procedure.
 13. A warmed TUBE CHANGER (or Eschmann Stylet), not shown, is carefully passed through the tube 269 into the trachea 112. If the tube changer will not pass through the ET tube connector then the connector must first be removed from the ET tube 269 before passage of the tube changer.
 14. With the tube changer (or stylet) and tube 269 securely in position, the airway 380 is carefully removed from the oral cavity 108 of the patient.
 15. If the tube 269 should come out of the trachea 112 during this maneuver, the inflatable cuff 288 is DEFLATED before proceeding further.
 16. The tube 269 is immediately advanced over the TUBE CHANGER (or stylet) back into the trachea 112.
 17. If it is necessary to ventilate the patient before the ET tube 269 is reinserted, a UNIVERSAL ET TUBE CONNECTOR is placed over the projecting end 360 of the breathing circuit elbow following which the proximal end of the TUBE CHANGER is inserted into the nipple 246 of the UNIVERSAL connector 240. Gentle ventilation is then resumed, following which the ET tube is reinserted into the trachea.

18. Following satisfactory ventilation the TUBE CHANGER (or stylet) is then removed. The ET tube connector is re-inserted into the ET tube 269, then connected to the oxygen supply. The cuff 288 is re-inflated and ventilation resumed.

19. Alternatively, the BRONCHOSCOP-AID 270 (with UNIVERSAL ET TUBE CONNECTORS 240 over each end) may be slipped over the ET tube 269 directly (without the ET tube connector in place) with oxygenation being provided via the BRONCHOSCOP-AID ventilating side arm 274, the upper port 240 on the upper end of the BRONCHOSCOP-AID 270 being plugged with a PLUG AND CAP unit 252, and the pressure relief port covered with tape to prevent gas loss.

In FIGS. 48–55 there is illustrated an oral airway 450 having a body 452 and a spline 454. The oral airway 450 has a pharyngeal segment 456, a dental contact zone 458 and a neck zone 460.

The dental contact zone 458 has a left front wall 462 and a right front wall 464.

The dental contact zone has a curved left side wall 466 and a curved right side wall 468 and a back wall 470.

In the dental contact zone 458 and the neck zone 460 there is a spline channel 472 having a left wall 474 and a keyway 476 in the left wall 474. The spline channel 472 has a right wall 478 and a right keyway 480 in the right wall 478.

The spline channel 472 has an airway central channel 482 with a posterior wall 484 at the back of the airway central channel 482.

In FIGS. 49 and 50 it is seen that there is a neck 486 having the neck airway central channel 488. The neck 486 has a left wall 474, left keyway 476, right wall 478, right keyway 480 and a posterior wall 484. In FIG. 48 and also in FIG. 50 there is illustrated a skid area 514 for the spline 454 to be in contact with the neck 486 and the dental contact zone 458.

In FIG. 48 there is illustrated in phantom line the left central channel wall 490 and the right channel wall 492.

The left central channel wall 490 and the curved left side wall 466 define the left lateral conduit 494.

The right central channel wall 492 and the curved right side wall 468 define a right lateral conduit 496.

In FIG. 54 there is illustrated a spline 454 having a main body 498 and a spline neck 500. The spline neck has a lip 502 on each side. With the spline 454 in the oral airway 450 the lip 502 is in contact with the skid area 514. The spline 454 has a key 504 on each side and on the inner part. There is a recess 506 between the lip 502 and the key 504.

In FIG. 56 at the left of the spline 454 there is illustrated a bevel 508. Also, it is seen that between the spline neck 500 and the main body 498 there is an abrupt edge 510.

In FIG. 48 it is seen that there is a spline channel 512. The spline 454 can be moved in the spline channel 512.

There is an upper left opening 516 and a lower left opening 518 connecting with the left lateral conduit 494.

There is an upper right opening 520 and a lower right opening 522 connecting with the right lateral conduit 496.

In FIGS. 48, 51 and 52 it is seen that there is a central channel outlet 524.

With the oral airway 380 and the spline 384 and with the oral airway 450 and the spline 454 it is possible to have a thin oral airway. In certain instances it is difficult to have a successful intubation. Prior to this invention if the intubation was difficult and not possible to place the large diameter tube into the oral cavity and trachea of the patient then it might be necessary to pass the ET tube nasally into the trachea, or a retrograde technique for oral intubation might have to be resorted to, or finally, the patient's neck might have to be incised and a tracheostomy tube inserted through the incision into the patient's neck and thence into the patient's trachea. The reader can readily appreciate the value of a thin oral airway such as 380 or 450 for receiving a large diameter tube. The spline 384 can be removed from the oral airway 380 or the spline 454 can be removed from the oral airway 450 and a large diameter tube inserted through the oral airway and into the oral cavity and trachea of the patient and over the fiberoptic scope.

In FIG. 2 the oral airway 450 with the spline 454 can be used in place of the oral airway 270.

Since the use of the oral airway 150 has been explained in detail with respect to FIG. 1 the use of the oral airway 380 with the spline 384 will not be explained in detail as the oral airways 150 and 380 can be used interchangeably.

Likewise, since the use of the oral airway 270 in FIG. 2 has been explained in detail the use of the oral airway 450 with the spline 454 will not be explained in detail because the oral airways 270 and 450 can be used interchangeably. The lack of detailed explanation of the use of the airway 380 in FIG. 1 and the airway 450 in FIG. 2 is based on not being repetitious and in an effort to try and avoid redundancy.

In FIGS. 57–61 there is illustrated a depth-adjustable non-intubating, non-fiberoptic oral airway 530. This oral airway comprises a dental contact zone 532, a pharyngeal zone 534 and a gas commonality housing 535. The housing 535 has flat opposing sides. The dental contact zone has a front wall 536, a curved left side wall 538, a curved right side wall 540 and a rear wall 542.

The pharyngeal zone 534 has a front wall 544, a left side wall 546, a right side wall 548 and a rear wall 550. The pharyngeal zone 534 has a lower lip or lower end 552 and an outlet orifice 554.

The gas commonality housing 535 has a flat top 556.

In the dental contact zone 532 and in the housing 534 there is a left central channel wall 558 and a right central channel wall 560.

The left central channel wall 558 in conjunction with the front wall 536, left side wall 538 and the rear wall 542 defines a left internal conduit 562.

The right central channel wall 560 in conjunction with the front wall 536, curved right side wall 540 and the rear wall 542 defines a right internal conduit 564.

The left central channel wall 558 and the right central channel wall 560 in conjunction with the rear wall 542 and the front wall 536 defines a central channel 566.

The gas commonality housing 535 defines a confluence chamber 568 for the three channels, 562, 564 and 566 for the two-way flow of gases. The gas commonality housing 535 connects with a ventilating side arm 570. There is a passageway 572 in the side arm 570 and this passageway connects with the confluence chamber 568. The side arm 570 is for attachment to a breathing circuit elbow 536.

On the end of the gas commonality housing 535 as opposed to the side arm 570 end there is a stop 574 which in conjunction with the side arm 570 limits the downward movement of the airway in relation to the oral mask.

In the lower end of the left lateral conduit 562 there is an opening 576. In the lower end of the right lateral conduit 564 there is an opening 578.

In FIGS. 57 and 60 there is illustrated the oral mask 120 positioned on the oral airway 530. The oral mask 120 has been described.

The oral airway 530 precludes the use of a fiberoptic scope. The oral airway 530 may be used with electroconvulsive therapy if constructed of polyurethane or a non-toxic medical grade elastomer such as Kraton. Also, it can be used at the end of eye surgery or at the end of nose surgery where there is not sufficient area on the face of the patient to use a complete face mask such as the modified face mask 330. In nose surgery there may be packing in the nose which precludes the flow of gas in the nose if a full face mask such as 330 is used. Therefore, a combination of an oral mask, such as 120, and an oral airway such as 530, is used. In some instances, where there is plastic surgery on the nose, it is not possible to have a full face mask 330 and that means that an oral mask 120 is used. Sometimes with eye surgery there is a large protective dressing and/or eye shield over the eye or with nose surgery there is a dressing on the nose. It is not possible to have good contact between a face mask 330 and the skin of the patient. Also, it may be necessary to continue to ventilate the patient after the endotracheal tube has been removed if the patient's ventilation is inadequate. Since a face mask 330 cannot be used then the combination of the oral mask 120 and the oral airway 530 is used. The reader can readily understand that one of the advantages of this airway is that it is possible to stay away from the site of operation such as the eye or the nose. The oral mask 120 is used and does not come in contact with the eye or the region of the eye and does not come in contact with the nose.

The combination of the oral mask 120 and the oral airway 530 can be inserted into the oral cavity 108 of the head 100 of the patient, see FIG. 1, in the same manner as the combination of the oral airway 150 and oral mask 120 is illustrated and used. Since the technique is the same, the combination of the oral mask 120 and the oral airway 530 will not be repeated for the sake of brevity. Again, the reader is to understand that with the oral airway 530 there is not used an endotracheal tube 269 and there is not used a flexible fiberoptic scope 276. The combination of the oral mask 102 and the oral airway 530 can also be used for cardio-pulmonary resuscitation (CPR).

FIGS. 1 and 2 have been described and the same components have been given the same reference numerals. In FIG. 1, in the phantom line rectangle, to the left of and above the oral face mask 120, there is illustrated a standard ET tube connector 580. The ET tube connector 580 can be used in place of the middle connector 240 on the lower end of the fiberoptic bronchoscope adapter 270 as illustrated in the phantom line rectangle directly above the oral mask 120. The ET tube connector 580 is of unitary construction and is essentially a reducer. The connector 580 has a large tube 582 on one end and a small tube 584 on the other end. Between the two tubes 582 and 584 there is a shoulder 586. The large tube 582 tapers so that the upper end has a smaller diameter than the other end. The small tube 584 tapers so that the outer end has a smaller diameter than the inner end. The large tube 584 fits and slides tightly into the fiberoptic bronchoscope adapter 270. The small tube 584 fits and slides tightly into the endotracheal tube 269. In effect, it is seen that the unitary ET tube connector 580 is a reducer in going from the large diameter fiberoptic bronchoscope adapter 270 or a breathing circuit elbow to the small diameter endotracheal tube 269. The other components have, previously, been described and will not, presently, be described again in order to not be redundant.

I was a practicing anesthesiologist for over 30 years. With the benefit of this experience I have invented the subject oral airways, oral mask and face mask and the combination of these units. I consider my invention to be new and useful and unobvious.

The invention is new and unobvious as I know of no similar oral airways, oral mask and face mask. There are many disclosures relating to apparatus used by an anesthesiologist. None of these disclosures is the same as the subject matter of this patent application.

The invention is useful in the anesthetizing of a patient, intubation of a patient, and also as a teaching tool. In a foregoing part of this disclosure there is listed a number of objects of the invention which further bring to the attention of the reader the usefulness of the subject matter of this invention.

From the preceeding disclosure it is seen that I have provided a ventilating depth-adjustable oral airway comprising a dental contact zone; a pharyngeal segment; a neck zone; said dental contact zone; said pharyngeal segment and said neck zone being unitary; said oral airway having a central channel in said dental contact zone, said pharyngeal segment and said neck zone for the flow of fluid; in the outer part of the pharyngeal segment an opening connecting with the central channel for the flow of fluid; the outer part of said pharyngeal segment being curved to adapt to the oral cavity and the oropharynx of a patient; in the interior of said dental contact zone there are two spaced apart walls to define three passageways such as said central channel, and a conduit identified as a first conduit and a conduit identified as a second conduit; said three passageways are for fluid wherein the dimensions of said dental contact zone are greater than the dimensions of said neck zone and greater than the dimensions of said pharyngeal segment. One form of this airway comprises a ventilating side arm having a passageway connecting with said oral airway near said neck and near said dental contact zone; said first conduit and said second conduit being in said oral airway near said neck zone and said first conduit connecting with said passageway in said ventilating side arm; said second conduit connecting with an opening in said oral airway near said neck; a removable sealing means for said opening; said two spaced apart walls having apertures to allow the flow of fluid between said three passageways; and, said dental contact zone being between said pharyngeal segment and said neck zone. In another form said oral airway comprises said first conduit having an upper opening near said neck zone and a lower opening near said pharyngeal segment; said second conduit having an upper opening near said neck zone and a lower opening near said pharyngeal segment with said dental contact zone being between said pharyngeal segment and said neck zone; said central channel extending through said neck; said central channel being of such interior dimensions as to be capable of simultaneously receiving a flexible fiberoptic scope and a tracheal tube; and, said opening in said pharyngeal segment having dimensions to allow simultaneously said flexible fiberoptic scope, said tracheal tube to pass out of said pharyngeal segment. With another form said oral airway comprises a removable spline; said spline having a means identified as a first means; said neck zone and said dental contact zone having a means identified as a second means; said first means and said second means operatively connecting together to allow the relative positions of said spline and said dental contact zone to vary; said first conduit having an upper opening near said neck zone and a lower opening near said pharyngeal segment; said second conduit having an upper opening near said neck zone and a lower opening near said pharyngeal segment; said first means being keys; said second means being keyways; said dental contact zone being between said pharyngeal segment and said neck zone; said central channel extending through said neck; with said spline in said oral airway said central channel being of such interior dimensions as to be capable of receiving a flexible fiberoptic scope; said opening in said pharyngeal segment having dimensions as to allow said flexible fiberoptic scope to pass out of said pharyngeal segment; said opening in said pharyngeal segment having dimensions to allow said tracheal tube to pass out of said pharyngeal segment; and, said spline being capable of being removed from said keyways and from said dental contact zone and from said neck zone. A further modification reveals an oral airway comprising a ventilating side arm having a passageway connecting with said oral airway near said neck and near said dental contact zone; in the upper part of said dental contact zone and near said neck zone there being a cross-over communicating channel connecting with said ventilating side arm and with said three passageways; a removable spline; spline having a means identified as a first means; said neck zone and said dental contact zone having a means identified as a second means; said first means and said second means operatively connecting together to allow the relative positions of said spline and said dental contact zone to vary; said first conduit having an upper opening connecting with said communicating channel and a lower opening near said pharyngeal segment; said second conduit having an upper opening connecting with said communicating channel and a lower opening near said pharyngeal segment; said first means being keys; said second means being keyways; said dental contact zone being between said pharyngeal segment and said neck zone; said central channel extending through said neck; with said spline in said oral airway said central channel being of such interior dimensions as to be capable of receiving a flexible fiberoptic scope; said opening in said pharyngeal segment having dimensions as to allow said flexible fiberoptic scope to pass out of said pharyngeal segment; said opening in said pharyngeal segment having dimensions to allow said tracheal tube to pass out of said pharyngeal segment; and, said spline being capable of being removed from said keyways and from said dental contact zone and from said neck zone. A still further modification is directed to an oral airway comprising said neck zone being on the outer part of said dental contact zone and comprising a gas commonality housing; said gas commonality housing having an outwardly directed side arm; a passageway in said side arm; a confluence chamber in said gas commonality housing; said confluence chamber operatively connecting with said three passageways and said passageway in said side arms; said side arm being at an angle to the longitudinal axis of said oral airway; said first conduit having an upper opening connecting with said confluence chamber and a lower opening near said pharyngeal segment; said second conduit having an upper opening connecting with said confluence chamber and a lower opening near said pharyngeal segment; and, said central channel connecting with said confluence chamber. There is also disclosed an oral airway comprising said conduit having an upper opening near said neck zone and a lower opening near said pharyngeal segment; said second conduit having an upper opening near said neck zone and a lower opening near said pharyngeal segment; a removable spline; said spline having a means identified as a first means; said neck zone and said dental contact zone having a means identified as a second means; said first means and said second means operatively connecting together to allow the relative positions of said spline and said dental contact zone to vary; said first conduit having an upper opening connecting with said communicating channel and a lower opening near said pharyngeal segment; said second conduit having an upper opening connecting with said communicating channel and a lower opening near said pharyngeal segment; said first means being keys; said second means being keyways; said dental contact zone being between said pharyngeal segment and said neck zone; said central channel extending through said neck; said opening in said pharyngeal segment having dimensions as to allow said flexible fiberoptic scope to pass out of said pharyngeal segment; said opening in said pharyngeal segment having dimensions to allow said tracheal tube to pass out of said pharyngeal segment; and, said spline being capable of being removed from said keyways and from said dental contact zone and from said neck zone.

Further, I have disclosed an oral mask for fitting over the mouth and the peri-oral tissues of a patient and for receiving and for positioning an oral airway, said mask comprising a curved body having a side identified as a first curved side and a side identified as a second curved side; in the central part of said body there being an outwardly projecting central housing; an opening in said central housing; said oral mask in a front elevational view being of a generally elliptical configuration; a notch in one edge of said oral mask to accomodate the nose of the patient; a plurality of outwardly projecting pins on the convex surface of said body; a sealing means in said opening and operatively connecting with said body; and, said sealing means being an O-ring.

Further, I have also disclosed a face mask comprising a mask body having sides; said sides being of a configuration to define a rear mask chimney having a passageway; said sides being of a configuration to define a front airway chimney having a receiving channel; a flexible cushion operatively connecting with said mask body; said sides in the vicinity of said front airway chimney being of heavier construction and reinforced; in said reinforced region and in said receiving channel a means for receiving an O-ring; an O-ring positioned in said means; a cushion mount; said mask body operatively connecting with said cushion mount; said flexible cushion operatively connecting with said cushion mount; and, said cushion mount is an inflatable housing.

Further, I have disclosed a method for making a ventilating depth-adjustable oral airway comprising forming a dental contact zone; forming a pharyngeal segment; forming a neck zone; forming said dental contact zone, said pharyngeal segment and said neck zone to be unitary; forming a central channel in said dental contact zone, said pharyngeal segment and said neck zone for the flow of fluid; forming in the outer part of the pharyngeal segment an opening connecting with the central channel for the flow of fluid; curving the pharyngeal segment to adapt to the oral cavity and the oro-pharynx of a patient; and, forming in the interior of said dental contact zone two spaced walls to define three passageways such as said central channel and a conduit identified as a first conduit and a conduit identified as a second conduit withsaid three passageways being for fluid.

In addition, I have disclosed a method for making an oral mask for fitting over the mouth and the peri-oral tissues of a patient and for receiving and for positioning an oral airway and comprising forming a curved body having a side identified as a first curved side and a side identified as a second curved side; forming an outwardly projecting central housing in the central part of said curved body; forming an opening in said central housing; and, operatively connecting said sealing means with said body.

Also, I have disclosed a method for making a face mask comprising forming a mask body having sides; forming said sides in the configuration to define a rear mask chimney having a passageway; forming said sides in the configuration to define a front airway chimney having a receiving channel; and, operatively connecting together a flexible cushion and said mask body.

Finally, I have disclosed a ventilating depth-adjustable oral airway made by a method comprising forming a dental contact zone; forming a pharyngeal segment; forming a neck zone; forming said dental contact zone, said pharyngeal segment and said neck zone to be unitary; forming a central channel in said dental contact zone, said pharyngeal segment and said neck zone for the flow of fluid; forming in the outer part of the pharyngeal segment an opening connecting with the central channel for the flow of fluid; curving the pharyngeal segment to adapt to the oral cavity and the oro-pharynx of a patient; and, forming in the interior of said dental contact zone two spaced walls to define three passageways such as said central channel and said conduit identified as a first conduit and a conduit identified as a second conduit with said three passageways being for fluid.

In addition to providing a ventilating depth-adjustable oral airway comprising a dental contact zone, a pharyngeal segment of a neck zone I have also provided a ventilating, intubating, fiberoptic facilitating depth-adjustable oral ariway comprising a dental contact zone, a pharyngeal segment and a neck zone.

The applicant has knowledge of the following United States patents but does not have copies of these patents: U.S. Pat. Nos. 3,841,341; 3,874,377; 4,305,387; 4,300,550; 4,240,420; 3,683,908; and 3,057,347. Also, there is Great Britian's patent No. 893,721 and Norweigan patent No. 97,937.

The applicant is enclosing with this disclosure copies of the following U.S. Pat. Nos.:

| NAME | NUMBER |
| --- | --- |
| V. R. Bennett | 2,857,911 |
| Peter Aiming Cheng | 2,908,269 |
| P. Safar et al | 3,013,554 |

-continued

| NAME | NUMBER |
| --- | --- |
| J. G. Fountain | 3,039,469 |
| A. J. McGee | 3,057,347 |
| Norman S. White et al | 3,774,616 |
| Paul H. Blachly | 4,112,936 |
| Joseph Fisher | 4,211,234 |
| Dennis C. Mahoney | 4,222,378 |
| Gale E. Dryden | 4,256,099 |
| Blachly et al | 4,270,531 |
| Crandall et al | 4,315,505 |
| Donald J. Walski | 4,316,459 |
| R. Tudor Williams | 4,338,930 |
| Harry Bartlett | 4,360,017 |
| Watson et al | 4,446,864 |
| James O. Elam | 4,449,526 |
| Ernest Warncke | 4,470,413 |
| John A. Paoluccio et al | 4,535,765 |
| Eugene L. Heyden | 4,607,635 |

From the foregoing and having presented my invention what I claim is:

1. The combination of an oral ask for fitting over the mouth and the peri-oral tissues of a patient and a ventilating, intubating, fiberoptic-facilitating, depth-adjustable oral airway for accommodating devices such as an endotracheal tube, a flexible fiberoptic scope, a suction catheter wherein:
  A. said oral mask comprises:
    A. a curved body having a side identified as a first curved side and a side identified as a second curved side and a central part;
    B. In the central part of said curved body there being an outwardly projecting central housing;
    C. an opening in said central housing; and,
    D. a sealing means in said opening and operatively connecting with said central housing:
  B. said oral airway comprises:
    E. a dental contact zone;
    F. a pharynegeal segment having an upper part having a complete front wall and a lower part having a partial front wall;
    G. a neck zone tapering and decreasing in cross-sectional dimension upon moving away from said dental zone;
    H. said dental contact zone, said pharyngeal segment and said neck zone being unitary;
    I. said oral airway having an enclosed central channel in said dental contact zone, the upper part of said pharyngeal segment and said neck zone for the flow of fluid and of such dimensions as to be capable of simultaneously receiving a flexible fiberoptic scope and a tracheal tube;
    J. in the lower part of the pharyngeal segment an outlet orifice in the front wall connecting with the central channel for the flow of fluid wherein said outlet orifice has dimensions to allow simultaneous said flexible fiberoptic scope and said tracheal tube to pass out of said pharyngeal segment and with said flexible fiberoptic scope being positioned within said tracheal tube;
    K. the lower part of said pharynegeal segment being curved to adapt to the oral cavity and the oropharynx of a patient;
    L. said dental contact zone having a width dimension greater than a thickness dimension:
    M. in the interior of said dental contact zone there being two spaced apart walls to define three passageways such as said central channel for receiving an endotracheal tube, and two enclosed lateral channels identified as a first lateral conduit and a second lateral conduit;

N. said three passageways are for the flow of fluid;

O. said pharynegeal segment having a curved distal part having a concave anterior area;

P. said curved distal part being tapered to be of less thickness than most of the pharyngeal segment for ease of insertion into a patient's mouth;

Q. said oral airway having an outwardly directed ventilating side arm having a passageway operatively connecting with at least one of said three passageways;

R. said ventilating side arm tapering and decreasing in cross-sectional dimension upon moving away from said dental contact zone;

C. said combination comprises:

S. said oral airway being adjustably positioned in said sealing means in said opening in said oral mask; and T. said side arm preventing movement of said oral mask onto said neck zone while allowing movement of said oral mask on said dental contact zone.

2. The combination of an oral mask according to claim 1 and comprising:
A. the width of said dental contact zone being greater than the width of said neck zone and being greater than the width of said pharyngeal segment; and,
B. said oral mask in a front elevational view being of a generally elliptical configuration.

3. The combination of an oral mask according to claim 1 and comprising:
A. said sealing means being an O-ring;
B. said O-ring providing a functional connection between said mask and said airway;
C. said oral mask, in a front elevational view being of a generally elliptical configuration;
D. a notch in one edge of said oral mask to accommodate the nose of the patient;
E. said oral mask having an inner concave surface and an outer convex surface; and,
F. a plurality of outwardly projecting pins of the outer convex surface of said body.

4. The combination of an oral mask according to claim 1 and comprising:
A. the width of said dental contact zone being greater than the width of said neck zone and being greater than the width of said pharyngeal segment;
B. said curved body having a concave inner surface;
C. a face cushion of the concave inner surface of the body; and,
D. said face cushion and said oral mask being capable of being separated.

5. The combination of an oral mask according to claim 1 and comprising:
A. said sealing means being an O-ring to allow a flexible adjustable arrangement between said oral mask and said oral airway for receiving and for positioning said oral airway;
B. said oral mask in a front elevational view being of a generally elliptical configuration; and,
C. a notch to one edge of said oral mask to accommodate the nose of the patient.

6. The combination of an oral mask and an oral airway according to claim 1 and comprising:
A. said dental contact zone being between said neck zone and said pharyngeal segment:
B. said neck zone being adjacent to said dental contact zone and comprising a gas commonality housing and comprising an outwardly directed ventilating side arm with said side arm being a direct extension of said gas commonalty housing;
C. a passageway in said side arm;
D. a confluence chamber in said gas commonalty housing;
E. said confluence chamber operatively connecting with said three passageways and said passageway in said side arm; and,
F. said side arm being at an angle to the longitudinal axis of said oral airway.

7. The combination of an oral mask and an oral airway according to claim 6 and comprising:
A. said first conduit having an upper opening connecting with said confluence chamber and a lower opening commencing at the level of the upper end of said pharyngeal segment;
B. said second conduit having an upper opening connecting with said confluence chamber and a lower opening commencing at the level of the upper end of said pharyngeal segment; and,
C. said central channel connecting with said confluence chamber.

8. The combination of an oral mask and an oral airway according to claim 7 and comprising:
A. said oral airway being unitary.

9. The combination of an oral mask and an oral airway according to claim 1 and comprising:
A. said oral airway comprising a ventilating side arm juxtapositioned to said neck zone and to said dental contact zone and having a passageway connecting with said first conduit;
B. an adapter means connecting with said neck zone and with an endotracheal tube;
C. said endotracheal tube operatively connecting with a middle connector;
D. said middle connector operatively connecting with a fiberoptic bronchoscope adapter;
E. said fiberoptic bronchoscope adapter operatively connecting with an upper port;
F. said fiberoptic bronchoscope adapter comprising a side arm; and,
G. a breathing circuit elbow connecting with said ventilating side arm and operatively connecting with a breathing circuit Y-piece.

10. The combination of an oral mask and an oral airway according to claim 9 and comprising:
A. said middle connector being a universal ET tube connector.

11. The combination of an oral mask and an oral airway according to claim 9 and comprising:
A. said middle connector being a standard ET tube connector.

12. The combination of an oral mask and an oral airway according to claim 9 and comprising:
A. a fiberoptic scope being positioned in said upper port, said fiberoptic bronchoscope adapter, said middle connector, said endotracheal tube and said central channel;
B. said side arm having a passageway; and,
C. the cap end of a plug and cap unit operatively connecting with and selectively covering said side arm and passageway.

13. The combination of an oral mask and an oral airway according to claim 1 and comprising:
A. said oral airway comprising a ventilating side arm juxtapositioned to said neck zone and having a passageway connecting with said first conduit; and, B. the cap end of a plug and cap unit operatively connecting with and selectively covering said ventilating side arm.

14. The combination of an oral airway and an oral mask according to claim 1 and comprising:
    A. said oral airway comprising a ventilating side arm juxtapositioned to said neck zone and having a passageway connecting with said first conduit;
    B. an adapter means connecting with said neck zone and with an endotracheal tube;
    C. said adapter means having an expansible port; and,
    D. the plug end of a plug and cap unit operatively connecting with and selectively sealing said expansible port.

15. The combination of an oral airway and an oral mask according to claim 1 and comprising:
    A. said oral airway comprising a ventilating side arm juxtapositioned to said neck zone and having a passageway connecting with said first conduit;
    B. an adapter means connecting with said neck zone and with an endotracheal tube;
    C. said endotracheal tube operatively connecting with a middle connector;
    D. said middle connector operatively connecting with a fiberoptic bronchoscope adapter:
    E. said fiberoptic bronchoscope adapter operatively connecting with an upper port;
    F. said upper port having an expansible port; and,
    G. the plug end of said plug and cap unit operatively connecting with and selectively sealing said expansible port.

16. The combination of an oral airway and an oral mask according to claim 1 and comprising:
    A. said oral airway comprising a ventilating side arm juxtapositioned to said neck zone and having a passageway connecting with said first conduit;
    B. an adapter means connecting with said neck zone and with an endotracheal tube;
    C. a standard ET tube connector operatively connecting with said endotracheal tube;
    D. said standard ET tube connector having a passageway; and,
    E. the cap end of said plug and cap unit operatively connecting with and selectively sealing said passageway.

17. The combination of an oral mask and an oral airway according to claim 1 and comprising:
    A. a ventilating side arm having a passageway connecting with said oral airway near said neck and near said dental contact zone;
    B. in the rear upper part of said airway between said dental contact zone and said neck there being a posteriorly enlarged housing the walls of which define a cross-over communicating channel connecting with said ventilating side arm and with said three passageways;
    C. a removable spine;
    D. said spine having a means identified as a first means;
    E. said neck zone and said dental contact zone having a means identified as a second means;
    F. said first means and said second means operatively connecting together to allow the relative positions of said spine and said dental contact zone to vary;
    G. said first conduit having an upper internal opening connecting with said cross-over communicating channel and a lower externally directed opening at the level of the upper end of said pharynegeal segment; and,
    H. said second conduit having an upper opening connecting with said cross-over communicating channel and a lower externally directed opening at the level of the upper end of said pharynegeal segment.

18. The combination of an oral mask and an oral airway according to claim 17 and comprising:
    A. said first means being keys;
    B. said second means being keyways; and,
    C. said dental contact zone being between said pharyngeal segment and said posteriorly-enlarged cross-over communicating channel housing.

19. The combination of an oral mask and an oral airway according to claim 18 and comprising:
    A. said central channel extending through said neck;
    B. with said spline in said oral airway said central channel being of such interior dimensions as to be capable of receiving a flexible fiberoptic scope;
    C. said opening in said pharyngeal segment having dimensions as to allow said flexible fiberoptic scope to pass out of said pharyngeal segment;
    D. said opening in said pharyngeal segment having dimensions to allow said tracheal tube to pass out of said pharyngeal segment; and,
    E. said spline being capable of being removed from said keyways and form said dental contact zone and from said neck zone.

20. The combination of an oral mask and an oral airway according to claim 18 and comprising:
    A. said central channel extending through said neck;
    B. with said oral airway being free of said spline said oral airway being capable of simultaneously receiving a flexible fiberoptic scope an a tracheal tube; and,
    C. with said oral airway being free of said spline said opening in said pharyngeal segment having dimensions as to allow simultaneously said flexible fiberoptic scope and said tracheal tube to pass out of said pharyngeal segment and with said flexible fiberoptic scope being positioned within said tracheal tube.

21. The combination of a face mask for fitting over the mouth and nose of a patient and a ventilating, intubating, depth-adjustable, fiberoptic-facilitating oral airway for accommodating an endotracheal tube wherein:
    A. said face mask comprises:
        A. a mask body having sides;
        B. said sides in the posterior region of the mask body being of a configuration to define a rear mask chimney having a first passageway;
        C. said sides in the anterior region of the mask body being of heavier construction and reinforced and being of a configuration to define a second passageway;
        D. said second passageway being an airway receiving channel;
        E. said sides in the airway-receiving channel having means to receive an O-ring;
        F. said O-ring providing a functional connection between said mask and said airway;
        G. an adjustable flexible cushion operatively connecting with said mask body;
    B. said oral airway comprises:
        H. a dental contact zone;
        I. a pharyngeal segment having a lower part having a partial front wall, and an upper part having a complete front wall;

J. a neck zone;

K. said dental contact zone, said pharyngeal segment and said neck zone being unitary;

L. said oral airway having an enclosed central channel in said dental contact zone, the upper part of said pharyngeal segment and said neck zone for the flow of fluid;

M. said pharyngeal segment having a curved distal part having a concave anterior area;

N. in the lower anterior area of the curved distal part of the pharyngeal segment an outlet orifice in the front wall connections with the central channel for the flow of fluid;

O. said curved distal part being tapered to be of less thickness than most of the pharyngeal segment for ease of insertion into a patient's mouth;

P. said dental contact zone having a width dimension greater than the thickness dimension;

Q. in the interior of said dental contact zone there are two spaced apart walls to define three passageways such as said central channel for receiving an endotracheal tube, and two enclosed lateral conduits identified as a first lateral conduit and a second lateral conduit;

R. said three passageways are for the flow of fluid; and,

S. said oral airway being operatively positioned in said front airway chimney.

22. A combination of a face mask according to claim 21 and comprising:

A. the lateral dimensions of said dental contact zone are greater than the lateral dimensions of said neck zone and greater than the lateral dimensions of said pharyngeal segment.

23. A combination of a face mask according to claim 22 and comprising:

A. said first conduit having an upper opening near said neck zone and a lower opening at the level of the upper end of said pharyngeal segment; and, B. said second conduit having an upper opening near said neck zone and a lower opening at the level of the upper end of said pharyngeal segment.

24. A combination of a face mask according to claim 23 and comprising:

A. said dental contact zone being between said pharyngeal segment and said neck zone.

25. A combination of a face mask according to claim 24 and comprising:

A. said central channel extending through said neck;

B. said central channel being of such interior dimensions as to be capable of simultaneously receiving a flexible fiberoptic scope and a tracheal tube; and, C. said opening in said pharyngeal segment having dimensions to allow simultaneously said flexible fiberoptic scope, and said tracheal tube to pass out of said pharyngeal segment and with said flexible fiberoptic scope being positioned within said tracheal tube.

26. A combination of a face mask according to claim 25 and comprising:

A. said airway being unitary.

27. A combination of a face mask according to claim 21 and comprising:

A. a removable spline;

B. said spline having a means identified as a first means;

C. said neck zone and said dental contact zone having a means identified as a second means;

D. said first means and said second means operatively connecting together to allow the relative positions of said spline and said dental contact zone to vary;

E. said first conduit having an upper opening near said neck zone and a lower opening at the level of the upper end of said pharyngeal segment; and, F. said second conduit having an upper opening near said neck zone and a lower opening at the level of the upper end of said pharyngeal segment.

28. A combination of a face mask according to claim 27 and comprising:

A. said first means being keys;

B. said second means being keyways; and,

C. said dental contact zone being between said pharyngeal segment and said neck zone.

29. A combination of a face mask according to claim 28 and comprising:

A. said central channel extending through said neck;

B. with said spline in said oral airway said central channel being of such interior dimensions as to be capable of receiving a flexible fiberoptic scope;

C. said opening in said pharyngeal segment having dimensions as to allow said flexible fiberoptic scope to pass out of said pharyngeal segment;

D. said opening in said pharyngeal segment having dimensions to allow said tracheal tube to pass out of said pharyngeal segment; and, E. said spline being capable of being removed from said keyways and from said dental contact zone and from said neck zone.

30. A combination of a face mask according to claim 28 and comprising:

A. said central channel extending through said neck;

B. with said oral airway being free of said spline said oral airway being capable of simultaneously receiving a flexible fiberoptic scope and a tracheal tube; and, C. with said oral airway being free of said spine said opening in said pharyngeal segment having dimensions to allow simultaneously said flexible fiberoptic scope and said tracheal tube to pass out of said pharyngeal segment and with said flexible fiberoptic scope being positioned within said tracheal tube.

* * * * *